US012636062B2

(12) United States Patent
Johnston et al.

(10) Patent No.: US 12,636,062 B2
(45) Date of Patent: May 26, 2026

(54) MULTIPLEXED HAND SWITCHES FOR USE WITH ELECTROSURGICAL GENERATORS

(71) Applicant: Covidien LP, Mansfield, MA (US)

(72) Inventors: Mark A. Johnston, Boulder, CO (US); Lewis R. Puterbaugh, Longmont, CO (US)

(73) Assignee: Covidien LP, Mansfield, MA (US)

( * ) Notice: Subject to any disclaimer, the term of this patent is extended or adjusted under 35 U.S.C. 154(b) by 873 days.

(21) Appl. No.: 17/742,516

(22) Filed: May 12, 2022

(65) Prior Publication Data

US 2022/0387093 A1 Dec. 8, 2022

Related U.S. Application Data

(60) Provisional application No. 63/197,534, filed on Jun. 7, 2021.

(51) Int. Cl.
*A61B 18/14* (2006.01)
*A61B 18/12* (2006.01)
*A61B 18/00* (2006.01)

(52) U.S. Cl.
CPC ...... *A61B 18/1206* (2013.01); *A61B 18/1445* (2013.01); *A61B 2018/0063* (2013.01); *A61B 2018/00696* (2013.01); *A61B 2018/00922* (2013.01); *A61B 2018/00958* (2013.01); *A61B 2018/1266* (2013.01)

(58) Field of Classification Search
CPC ............ A61B 18/1445; A61B 18/1442; A61B 2018/00922; A61B 2018/00958
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,693,106 A | 11/1954 | Henry |
| 2,827,056 A | 3/1958 | Degelman |
| 2,849,611 A | 8/1958 | Adams |
| 2,883,198 A | 4/1959 | Narumi |
| 3,001,132 A | 9/1961 | Britt |

(Continued)

FOREIGN PATENT DOCUMENTS

| | | |
|---|---|---|
| DE | 179607 C | 11/1906 |
| DE | 390937 C | 3/1924 |

(Continued)

OTHER PUBLICATIONS

US 6,878,148 B2, 04/2005, Goble et al. (withdrawn)

(Continued)

*Primary Examiner* — Sean W Collins

(57) ABSTRACT

An electrosurgical system includes an electrosurgical device having: a main switch, a button configured to actuate the main switch, at least one secondary switch, and a movable component configured to actuate the second switch. The system also includes an electrosurgical generator coupled to the electrosurgical device, the electrosurgical generator is configured to generate an electrosurgical output in response to actuation of the main switch and the at least one secondary switch.

18 Claims, 5 Drawing Sheets

| 0=switch Open | | | |
|---|---|---|---|
| 1=switch Closed | | | |
| | | | |
| Switch | | | |
| Activation | Jaw aperture | Lever | Instrument State |
| 0 | 0 | 0 | Activation off |
| 0 | 0 | 1 | Activation off |
| 0 | 1 | 0 | Activation off |
| 0 | 1 | 1 | Activation off |
| 1 | 0 | 0 | Activation on. jaw and lever open |
| 1 | 0 | 1 | Activation on. jaw open and lever closed |
| 1 | 1 | 0 | Activation on. jaw closed and lever open |
| 1 | 1 | 1 | Activation on. jaw and lever closed |

(56) References Cited

U.S. PATENT DOCUMENTS

| | | |
|---|---|---|
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,118,700 A | 10/1978 | Lenihan |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |

(56)                References Cited

U.S. PATENT DOCUMENTS

| | | | |
|---|---|---|---|
| 4,739,759 | A | 4/1988 | Rexroth et al. |
| 4,741,334 | A | 5/1988 | Irnich |
| 4,741,348 | A | 5/1988 | Kikuchi et al. |
| 4,744,372 | A | 5/1988 | Kikuchi et al. |
| 4,754,757 | A | 7/1988 | Feucht |
| 4,767,999 | A | 8/1988 | VerPlanck |
| 4,768,969 | A | 9/1988 | Bauer et al. |
| 4,785,829 | A | 11/1988 | Convert et al. |
| 4,788,634 | A | 11/1988 | Schlecht et al. |
| 4,805,621 | A | 2/1989 | Heinze et al. |
| 4,818,954 | A | 4/1989 | Flachenecker et al. |
| 4,827,927 | A | 5/1989 | Newton |
| 4,848,335 | A | 7/1989 | Manes |
| 4,860,745 | A | 8/1989 | Farin et al. |
| 4,862,889 | A | 9/1989 | Feucht |
| 4,887,199 | A | 12/1989 | Whittle |
| 4,890,610 | A | 1/1990 | Kirwan, Sr. et al. |
| 4,903,696 | A | 2/1990 | Stasz et al. |
| 4,907,589 | A | 3/1990 | Cosman |
| 4,922,210 | A | 5/1990 | Flachenecker et al. |
| 4,925,089 | A | 5/1990 | Chaparro et al. |
| 4,931,047 | A | 6/1990 | Broadwin et al. |
| 4,931,717 | A | 6/1990 | Gray et al. |
| 4,938,761 | A | 7/1990 | Ensslin |
| 4,942,313 | A | 7/1990 | Kinzel |
| 4,959,606 | A | 9/1990 | Forge |
| 4,961,047 | A | 10/1990 | Carder |
| 4,961,435 | A | 10/1990 | Kitagawa et al. |
| 4,966,597 | A | 10/1990 | Cosman |
| 4,969,885 | A | 11/1990 | Farin |
| 4,992,719 | A | 2/1991 | Harvey |
| 4,993,430 | A | 2/1991 | Shimoyama et al. |
| 4,995,877 | A | 2/1991 | Ams et al. |
| 5,015,227 | A | 5/1991 | Broadwin et al. |
| 5,024,668 | A | 6/1991 | Peters et al. |
| 5,044,977 | A | 9/1991 | Vindigni |
| 5,057,105 | A | 10/1991 | Malone et al. |
| 5,067,953 | A | 11/1991 | Feucht |
| 5,075,839 | A | 12/1991 | Fisher et al. |
| 5,078,153 | A | 1/1992 | Nordlander et al. |
| 5,087,257 | A | 2/1992 | Farin et al. |
| 5,099,840 | A | 3/1992 | Goble et al. |
| 5,103,804 | A | 4/1992 | Abele et al. |
| 5,108,389 | A | 4/1992 | Cosmescu |
| 5,108,391 | A | 4/1992 | Flachenecker et al. |
| 5,113,116 | A | 5/1992 | Wilson |
| 5,119,284 | A | 6/1992 | Fisher et al. |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,161,893 | A | 11/1992 | Shigezawa et al. |
| 5,167,658 | A | 12/1992 | Ensslin |
| 5,167,659 | A | 12/1992 | Ohtomo et al. |
| 5,190,517 | A | 3/1993 | Zieve et al. |
| 5,196,008 | A | 3/1993 | Kuenecke et al. |
| 5,196,009 | A | 3/1993 | Kirwan, Jr. |
| 5,201,900 | A | 4/1993 | Nardella |
| 5,207,691 | A | 5/1993 | Nardella |
| 5,216,338 | A | 6/1993 | Wilson |
| 5,230,623 | A | 7/1993 | Guthrie et al. |
| 5,233,515 | A | 8/1993 | Cosman |
| 5,234,427 | A | 8/1993 | Ohtomo et al. |
| 5,244,462 | A | 9/1993 | Delahuerga et al. |
| 5,249,121 | A | 9/1993 | Baum et al. |
| 5,249,585 | A | 10/1993 | Turner et al. |
| 5,254,117 | A | 10/1993 | Rigby et al. |
| RE34,432 | E | 11/1993 | Bertrand |
| 5,267,994 | A | 12/1993 | Gentelia et al. |
| 5,267,997 | A | 12/1993 | Farin et al. |
| 5,269,780 | A | 12/1993 | Roos |
| 5,271,413 | A | 12/1993 | Dalamagas et al. |
| 5,281,213 | A | 1/1994 | Milder et al. |
| 5,282,840 | A | 2/1994 | Hudrlik |
| 5,290,283 | A | 3/1994 | Suda |
| 5,295,857 | A | 3/1994 | Toly |
| 5,300,068 | A | 4/1994 | Rosar et al. |
| 5,300,070 | A | 4/1994 | Gentelia et al. |
| 5,304,917 | A | 4/1994 | Somerville |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,183 | A | 8/1994 | Wuchinich |
| 5,334,193 | A | 8/1994 | Nardella |
| 5,341,807 | A | 8/1994 | Nardella |
| 5,342,356 | A | 8/1994 | Ellman et al. |
| 5,342,357 | A | 8/1994 | Nardella |
| 5,342,409 | A | 8/1994 | Mullett |
| 5,346,406 | A | 9/1994 | Hoffman et al. |
| 5,346,491 | A | 9/1994 | Oertli |
| 5,348,554 | A | 9/1994 | Imran et al. |
| 5,354,325 | A | 10/1994 | Chive et al. |
| 5,364,392 | A | 11/1994 | Warner et al. |
| 5,369,567 | A | 11/1994 | Furuta et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson et al. |
| 5,383,876 | A | 1/1995 | Nardella |
| 5,383,917 | A | 1/1995 | Desai et al. |
| 5,385,148 | A | 1/1995 | Lesh et al. |
| 5,396,194 | A | 3/1995 | Williamson et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,485 | A | 4/1995 | Suda |
| 5,413,573 | A | 5/1995 | Koivukangas |
| 5,414,238 | A | 5/1995 | Steigerwald et al. |
| 5,417,719 | A | 5/1995 | Hull et al. |
| 5,422,567 | A | 6/1995 | Matsunaga |
| 5,422,926 | A | 6/1995 | Smith et al. |
| 5,423,808 | A | 6/1995 | Edwards et al. |
| 5,423,809 | A | 6/1995 | Klicek |
| 5,423,810 | A | 6/1995 | Goble et al. |
| 5,423,811 | A | 6/1995 | Imran et al. |
| 5,425,704 | A | 6/1995 | Sakurai et al. |
| 5,429,596 | A | 7/1995 | Arias et al. |
| 5,430,434 | A | 7/1995 | Lederer et al. |
| 5,432,459 | A | 7/1995 | Thompson et al. |
| 5,433,739 | A | 7/1995 | Sluijter et al. |
| 5,436,566 | A | 7/1995 | Thompson et al. |
| 5,438,302 | A | 8/1995 | Goble |
| 5,443,462 | A | 8/1995 | Hannant |
| 5,443,463 | A | 8/1995 | Stern et al. |
| 5,445,635 | A | 8/1995 | Denen et al. |
| 5,445,638 | A | 8/1995 | Rydell et al. |
| 5,448,466 | A | 9/1995 | Erckert |
| 5,451,224 | A | 9/1995 | Goble et al. |
| 5,452,725 | A | 9/1995 | Martenson |
| 5,454,809 | A | 10/1995 | Janssen |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,474,464 | A | 12/1995 | Drewnicki |
| 5,480,399 | A | 1/1996 | Hebborn |
| 5,483,952 | A | 1/1996 | Aranyi |
| 5,485,312 | A | 1/1996 | Horner et al. |
| 5,496,312 | A | 3/1996 | Klicek |
| 5,496,313 | A | 3/1996 | Gentelia et al. |
| 5,496,314 | A | 3/1996 | Eggers |
| 5,498,261 | A | 3/1996 | Strul |
| 5,500,012 | A | 3/1996 | Brucker et al. |
| 5,500,616 | A | 3/1996 | Ochi |
| 5,511,993 | A | 4/1996 | Yamada et al. |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |

(56) References Cited

U.S. PATENT DOCUMENTS

| | | | |
|---|---|---|---|
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |
| 5,542,916 A | 8/1996 | Hirsch et al. |
| 5,545,161 A | 8/1996 | Imran |
| 5,554,172 A | 9/1996 | Horner et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,693,082 A | 12/1997 | Warner et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,835 A | 8/1999 | Mackey |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,002,968 A | 12/1999 | Edwards |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |
| 6,055,458 A | 4/2000 | Cochran et al. |

(56)        References Cited

U.S. PATENT DOCUMENTS

| | | | |
|---|---|---|---|
| 6,056,745 | A | 5/2000 | Panescu et al. |
| 6,056,746 | A | 5/2000 | Goble et al. |
| 6,059,780 | A | 5/2000 | Gough et al. |
| 6,059,781 | A | 5/2000 | Yamanashi et al. |
| 6,063,075 | A | 5/2000 | Mihori |
| 6,063,078 | A | 5/2000 | Wittkampf |
| 6,066,137 | A | 5/2000 | Greep |
| 6,068,627 | A | 5/2000 | Orszulak et al. |
| 6,074,089 | A | 6/2000 | Hollander et al. |
| 6,074,386 | A | 6/2000 | Goble et al. |
| 6,074,388 | A | 6/2000 | Tockweiler et al. |
| 6,080,149 | A | 6/2000 | Huang et al. |
| 6,088,614 | A | 7/2000 | Swanson |
| 6,089,864 | A | 7/2000 | Buckner et al. |
| 6,090,123 | A | 7/2000 | Culp et al. |
| 6,093,186 | A | 7/2000 | Goble |
| 6,102,497 | A | 8/2000 | Ehr et al. |
| 6,102,907 | A | 8/2000 | Smethers et al. |
| 6,104,248 | A | 8/2000 | Carver |
| 6,106,524 | A | 8/2000 | Eggers et al. |
| 6,113,591 | A | 9/2000 | Whayne et al. |
| 6,113,592 | A | 9/2000 | Taylor |
| 6,113,593 | A | 9/2000 | Tu et al. |
| 6,113,596 | A | 9/2000 | Hooven et al. |
| 6,123,701 | A | 9/2000 | Nezhat |
| 6,123,702 | A | 9/2000 | Swanson et al. |
| 6,132,429 | A | 10/2000 | Baker |
| 6,139,349 | A | 10/2000 | Wright |
| 6,142,992 | A | 11/2000 | Cheng et al. |
| 6,144,937 | A | 11/2000 | Ali |
| 6,155,975 | A | 12/2000 | Urich et al. |
| 6,162,184 | A | 12/2000 | Swanson et al. |
| 6,162,217 | A | 12/2000 | Kannenberg et al. |
| 6,165,169 | A | 12/2000 | Panescu et al. |
| 6,165,173 | A | 12/2000 | Kamdar et al. |
| 6,171,304 | B1 | 1/2001 | Netherly |
| 6,173,713 | B1 | 1/2001 | Dawson |
| 6,183,468 | B1 | 2/2001 | Swanson et al. |
| 6,186,147 | B1 | 2/2001 | Cobb |
| 6,188,211 | B1 | 2/2001 | Rincon-Mora et al. |
| 6,193,713 | B1 | 2/2001 | Geistert et al. |
| 6,197,023 | B1 | 3/2001 | Muntermann |
| 6,200,314 | B1 | 3/2001 | Sherman |
| 6,203,541 | B1 | 3/2001 | Keppel |
| 6,210,403 | B1 | 4/2001 | Klicek |
| 6,216,704 | B1 | 4/2001 | Ingle et al. |
| 6,222,356 | B1 | 4/2001 | Taghizadeh-Kaschani |
| 6,228,078 | B1 | 5/2001 | Eggers et al. |
| 6,228,080 | B1 | 5/2001 | Gines |
| 6,228,081 | B1 | 5/2001 | Goble |
| 6,231,569 | B1 | 5/2001 | Bek et al. |
| 6,232,556 | B1 | 5/2001 | Daugherty et al. |
| 6,235,020 | B1 | 5/2001 | Cheng et al. |
| 6,235,022 | B1 | 5/2001 | Hallock et al. |
| 6,237,604 | B1 | 5/2001 | Burnside et al. |
| 6,238,387 | B1 | 5/2001 | Miller, III |
| 6,238,388 | B1 | 5/2001 | Ellman et al. |
| 6,241,723 | B1 | 6/2001 | Heim et al. |
| 6,241,725 | B1 | 6/2001 | Cosman |
| 6,243,654 | B1 | 6/2001 | Johnson et al. |
| 6,245,061 | B1 | 6/2001 | Panescu et al. |
| 6,245,063 | B1 | 6/2001 | Uphoff |
| 6,245,065 | B1 | 6/2001 | Panescu et al. |
| 6,246,912 | B1 | 6/2001 | Sluijter et al. |
| 6,251,106 | B1 | 6/2001 | Becker et al. |
| 6,254,422 | B1 | 7/2001 | Feye-Hohmann |
| 6,258,085 | B1 | 7/2001 | Eggleston |
| 6,259,937 | B1 | 7/2001 | Schulman et al. |
| 6,261,285 | B1 | 7/2001 | Novak et al. |
| 6,261,286 | B1 | 7/2001 | Goble et al. |
| 6,267,760 | B1 | 7/2001 | Swanson |
| 6,270,497 | B1 | 8/2001 | Sekino et al. |
| 6,273,886 | B1 | 8/2001 | Edwards et al. |
| 6,275,786 | B1 | 8/2001 | Daners |
| 6,287,304 | B1 | 9/2001 | Eggers et al. |
| 6,293,941 | B1 | 9/2001 | Strul et al. |
| 6,293,942 | B1 | 9/2001 | Goble et al. |
| 6,293,943 | B1 | 9/2001 | Panescu et al. |
| 6,296,636 | B1 | 10/2001 | Cheng et al. |
| 6,304,138 | B1 | 10/2001 | Johnson |
| 6,306,131 | B1 | 10/2001 | Hareyama et al. |
| 6,306,134 | B1 | 10/2001 | Goble et al. |
| 6,309,386 | B1 | 10/2001 | Bek |
| 6,322,558 | B1 | 11/2001 | Taylor et al. |
| 6,325,799 | B1 | 12/2001 | Goble |
| 6,329,778 | B1 | 12/2001 | Culp et al. |
| 6,337,998 | B1 | 1/2002 | Behl et al. |
| 6,338,657 | B1 | 1/2002 | Harper et al. |
| 6,341,981 | B1 | 1/2002 | Gorman |
| 6,350,262 | B1 | 2/2002 | Ashley |
| 6,350,263 | B1 | 2/2002 | Wetzig et al. |
| 6,358,245 | B1 | 3/2002 | Edwards et al. |
| 6,364,877 | B1 | 4/2002 | Goble et al. |
| 6,370,408 | B1 | 4/2002 | Merchant et al. |
| 6,371,963 | B1 | 4/2002 | Nishtala et al. |
| 6,383,183 | B1 | 5/2002 | Sekino et al. |
| 6,387,092 | B1 | 5/2002 | Burnside et al. |
| 6,391,024 | B1 | 5/2002 | Sun et al. |
| 6,398,779 | B1 | 6/2002 | Buysse et al. |
| 6,398,781 | B1 | 6/2002 | Goble et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,722 | B1 | 6/2002 | Hoey et al. |
| 6,413,256 | B1 | 7/2002 | Truckai et al. |
| 6,416,509 | B1 | 7/2002 | Goble et al. |
| 6,422,896 | B2 | 7/2002 | Aoki et al. |
| 6,423,057 | B1 | 7/2002 | He et al. |
| 6,424,186 | B1 | 7/2002 | Quimby et al. |
| 6,426,886 | B1 | 7/2002 | Goder |
| 6,427,089 | B1 | 7/2002 | Knowlton |
| 6,428,537 | B1 | 8/2002 | Swanson et al. |
| 6,436,096 | B1 | 8/2002 | Hareyama |
| 6,440,157 | B1 | 8/2002 | Shigezawa et al. |
| 6,451,015 | B1 | 9/2002 | Rittman, III et al. |
| 6,454,594 | B2 | 9/2002 | Sawayanagi |
| 6,458,121 | B1 | 10/2002 | Rosenstock et al. |
| 6,458,122 | B1 | 10/2002 | Pozzato |
| 6,464,689 | B1 | 10/2002 | Qin et al. |
| 6,464,696 | B1 | 10/2002 | Oyama et al. |
| 6,468,270 | B1 | 10/2002 | Hovda et al. |
| 6,468,273 | B1 | 10/2002 | Leveen et al. |
| 6,469,481 | B1 | 10/2002 | Tateishi |
| 6,482,201 | B1 | 11/2002 | Olsen et al. |
| 6,485,487 | B1 | 11/2002 | Sherman |
| 6,488,678 | B2 | 12/2002 | Sherman |
| 6,494,880 | B1 | 12/2002 | Swanson et al. |
| 6,497,659 | B1 | 12/2002 | Rafert |
| 6,498,466 | B1 | 12/2002 | Edwards |
| 6,506,189 | B1 | 1/2003 | Rittman, III et al. |
| 6,508,815 | B1 | 1/2003 | Strul et al. |
| 6,511,476 | B2 | 1/2003 | Hareyama |
| 6,511,478 | B1 | 1/2003 | Burnside et al. |
| 6,514,251 | B1 | 2/2003 | Ni et al. |
| 6,517,538 | B1 | 2/2003 | Jacob et al. |
| 6,522,931 | B2 | 2/2003 | Manker et al. |
| 6,524,308 | B1 | 2/2003 | Muller et al. |
| 6,537,272 | B2 | 3/2003 | Christopherson et al. |
| 6,544,258 | B2 | 4/2003 | Fleenor et al. |
| 6,544,260 | B1 | 4/2003 | Markel et al. |
| 6,546,270 | B1 | 4/2003 | Goldin et al. |
| 6,547,786 | B1 | 4/2003 | Goble |
| 6,557,559 | B1 | 5/2003 | Eggers et al. |
| 6,558,376 | B2 | 5/2003 | Bishop |
| 6,558,377 | B2 | 5/2003 | Lee et al. |
| 6,560,470 | B1 | 5/2003 | Pologe |
| 6,562,037 | B2 | 5/2003 | Paton et al. |
| 6,565,559 | B2 | 5/2003 | Eggleston |
| 6,565,562 | B1 | 5/2003 | Shah et al. |
| 6,575,969 | B1 | 6/2003 | Rittman, III et al. |
| 6,578,579 | B2 | 6/2003 | Burnside et al. |
| 6,579,288 | B1 | 6/2003 | Swanson et al. |
| 6,582,427 | B1 | 6/2003 | Goble et al. |

(56)  References Cited

U.S. PATENT DOCUMENTS

| | | | |
|---|---|---|---|
| 6,602,243 | B2 | 8/2003 | Noda |
| 6,602,252 | B2 | 8/2003 | Mollenauer |
| 6,611,793 | B1 | 8/2003 | Burnside et al. |
| 6,620,157 | B1 | 9/2003 | Dabney et al. |
| 6,620,189 | B1 | 9/2003 | Machold et al. |
| 6,623,423 | B2 | 9/2003 | Sakurai et al. |
| 6,626,901 | B1 | 9/2003 | Treat et al. |
| 6,629,973 | B1 | 10/2003 | Wardell et al. |
| 6,629,974 | B2 | 10/2003 | Penny et al. |
| 6,632,193 | B1 | 10/2003 | Davison et al. |
| 6,635,056 | B2 | 10/2003 | Kadhiresan et al. |
| 6,635,057 | B2 | 10/2003 | Harano et al. |
| 6,645,198 | B1 | 11/2003 | Bommannan et al. |
| 6,648,883 | B2 | 11/2003 | Francischelli et al. |
| 6,651,669 | B1 | 11/2003 | Burnside |
| 6,652,513 | B2 | 11/2003 | Panescu et al. |
| 6,652,514 | B2 | 11/2003 | Ellman et al. |
| 6,653,569 | B1 | 11/2003 | Sung |
| 6,656,177 | B2 | 12/2003 | Truckai et al. |
| 6,663,623 | B1 | 12/2003 | Oyama et al. |
| 6,663,624 | B2 | 12/2003 | Edwards et al. |
| 6,663,627 | B2 | 12/2003 | Francischelli et al. |
| 6,666,860 | B1 | 12/2003 | Takahashi |
| 6,672,151 | B1 | 1/2004 | Schultz et al. |
| 6,679,875 | B2 | 1/2004 | Honda et al. |
| 6,682,527 | B2 | 1/2004 | Strul |
| 6,685,700 | B2 | 2/2004 | Behl et al. |
| 6,685,701 | B2 | 2/2004 | Orszulak et al. |
| 6,685,703 | B2 | 2/2004 | Pearson et al. |
| 6,689,131 | B2 | 2/2004 | McClurken |
| 6,692,489 | B1 | 2/2004 | Heim et al. |
| 6,693,782 | B1 | 2/2004 | Lash |
| 6,695,837 | B2 | 2/2004 | Howell |
| 6,696,844 | B2 | 2/2004 | Wong et al. |
| 6,700,076 | B2 | 3/2004 | Sun et al. |
| 6,712,813 | B2 | 3/2004 | Ellman et al. |
| 6,723,091 | B2 | 4/2004 | Goble et al. |
| 6,730,078 | B2 | 5/2004 | Simpson et al. |
| 6,730,079 | B2 | 5/2004 | Lovewell |
| 6,730,080 | B2 | 5/2004 | Harano et al. |
| 6,733,495 | B1 | 5/2004 | Bek et al. |
| 6,733,498 | B2 | 5/2004 | Paton et al. |
| 6,736,810 | B2 | 5/2004 | Hoey et al. |
| 6,740,079 | B1 | 5/2004 | Eggers et al. |
| 6,740,085 | B2 | 5/2004 | Hareyama et al. |
| 6,743,225 | B2 | 6/2004 | Sanchez et al. |
| 6,746,284 | B1 | 6/2004 | Spink, Jr. |
| 6,749,624 | B2 | 6/2004 | Knowlton |
| 6,755,825 | B2 | 6/2004 | Shoenman et al. |
| 6,758,846 | B2 | 7/2004 | Goble et al. |
| 6,761,716 | B2 | 7/2004 | Kadhiresan et al. |
| 6,775,575 | B2 | 8/2004 | Bommannan et al. |
| 6,778,044 | B2 | 8/2004 | Fehrenbach et al. |
| 6,783,523 | B2 | 8/2004 | Qin et al. |
| 6,784,405 | B2 | 8/2004 | Flugstad et al. |
| 6,786,905 | B2 | 9/2004 | Swanson et al. |
| 6,788,977 | B2 | 9/2004 | Fenn et al. |
| 6,790,206 | B2 | 9/2004 | Panescu |
| 6,792,390 | B1 | 9/2004 | Burnside et al. |
| 6,796,980 | B2 | 9/2004 | Hall |
| 6,796,981 | B2 | 9/2004 | Wham et al. |
| 6,809,508 | B2 | 10/2004 | Donofrio |
| 6,818,000 | B2 | 11/2004 | Muller et al. |
| 6,819,027 | B2 | 11/2004 | Saraf |
| 6,824,539 | B2 | 11/2004 | Novak |
| 6,830,569 | B2 | 12/2004 | Thompson et al. |
| 6,837,888 | B2 | 1/2005 | Ciarrocca et al. |
| 6,843,682 | B2 | 1/2005 | Matsuda et al. |
| 6,843,789 | B2 | 1/2005 | Goble |
| 6,849,073 | B2 | 2/2005 | Hoey et al. |
| 6,855,141 | B2 | 2/2005 | Lovewell |
| 6,855,142 | B2 | 2/2005 | Harano et al. |
| 6,860,881 | B2 | 3/2005 | Sturm et al. |
| 6,864,686 | B2 | 3/2005 | Novak et al. |
| 6,875,210 | B2 | 4/2005 | Refior et al. |
| 6,887,240 | B1 | 5/2005 | Lands et al. |
| 6,890,331 | B2 | 5/2005 | Kristensen |
| 6,893,435 | B2 | 5/2005 | Goble |
| 6,899,538 | B2 | 5/2005 | Matoba |
| 6,923,804 | B2 | 8/2005 | Eggers et al. |
| 6,929,641 | B2 | 8/2005 | Goble et al. |
| 6,936,047 | B2 | 8/2005 | Nasab et al. |
| 6,939,344 | B2 | 9/2005 | Kreindel |
| 6,939,346 | B2 | 9/2005 | Kannenberg et al. |
| 6,939,347 | B2 | 9/2005 | Thompson |
| 6,942,660 | B2 | 9/2005 | Pantera et al. |
| 6,948,503 | B2 | 9/2005 | Refior et al. |
| 6,953,461 | B2 | 10/2005 | McClurken et al. |
| 6,958,064 | B2 | 10/2005 | Rioux et al. |
| 6,962,587 | B2 | 11/2005 | Johnson et al. |
| 6,966,907 | B2 | 11/2005 | Goble |
| 6,970,752 | B1 | 11/2005 | Lim et al. |
| 6,974,453 | B2 | 12/2005 | Woloszko et al. |
| 6,974,463 | B2 | 12/2005 | Magers et al. |
| 6,977,495 | B2 | 12/2005 | Donofrio |
| 6,979,329 | B2 | 12/2005 | Burnside et al. |
| 6,984,231 | B2 | 1/2006 | Goble et al. |
| 6,989,010 | B2 | 1/2006 | Francischelli et al. |
| 6,994,704 | B2 | 2/2006 | Qin et al. |
| 6,994,707 | B2 | 2/2006 | Ellman et al. |
| 6,997,935 | B2 | 2/2006 | Anderson et al. |
| 7,001,379 | B2 | 2/2006 | Behl et al. |
| 7,001,381 | B2 | 2/2006 | Harano et al. |
| 7,004,174 | B2 | 2/2006 | Eggers et al. |
| 7,008,369 | B2 | 3/2006 | Cuppen |
| 7,008,417 | B2 | 3/2006 | Eick |
| 7,008,421 | B2 | 3/2006 | Daniel et al. |
| 7,025,764 | B2 | 4/2006 | Paton et al. |
| 7,033,351 | B2 | 4/2006 | Howell |
| 7,041,096 | B2 | 5/2006 | Malis et al. |
| 7,044,948 | B2 | 5/2006 | Keppel |
| 7,044,949 | B2 | 5/2006 | Orszulak et al. |
| 7,048,687 | B1 | 5/2006 | Reuss et al. |
| 7,058,372 | B1 | 6/2006 | Pardoen et al. |
| 7,060,063 | B2 | 6/2006 | Marion et al. |
| 7,062,331 | B2 | 6/2006 | Zarinetchi et al. |
| 7,063,692 | B2 | 6/2006 | Sakurai et al. |
| 7,066,933 | B2 | 6/2006 | Hagg |
| 7,074,217 | B2 | 7/2006 | Strul et al. |
| 7,083,618 | B2 | 8/2006 | Couture et al. |
| 7,087,054 | B2 | 8/2006 | Truckai et al. |
| 7,094,231 | B1 | 8/2006 | Ellman et al. |
| 7,104,834 | B2 | 9/2006 | Robinson et al. |
| RE39,358 | E | 10/2006 | Goble |
| 7,115,121 | B2 | 10/2006 | Novak |
| 7,115,124 | B1 | 10/2006 | Xiao |
| 7,118,564 | B2 | 10/2006 | Ritchie et al. |
| 7,122,031 | B2 | 10/2006 | Edwards et al. |
| 7,131,445 | B2 | 11/2006 | Amoah |
| 7,131,860 | B2 | 11/2006 | Sartor et al. |
| 7,137,980 | B2 | 11/2006 | Buysse et al. |
| 7,146,210 | B2 | 12/2006 | Palti |
| 7,147,638 | B2 | 12/2006 | Chapman et al. |
| 7,151,964 | B2 | 12/2006 | Desai et al. |
| 7,153,300 | B2 | 12/2006 | Goble |
| 7,156,842 | B2 | 1/2007 | Sartor et al. |
| 7,156,844 | B2 | 1/2007 | Reschke et al. |
| 7,156,846 | B2 | 1/2007 | Dycus et al. |
| 7,160,293 | B2 | 1/2007 | Sturm et al. |
| 7,163,536 | B2 | 1/2007 | Godara |
| 7,166,986 | B2 | 1/2007 | Kendall |
| 7,169,144 | B2 | 1/2007 | Hoey et al. |
| 7,172,591 | B2 | 2/2007 | Harano et al. |
| 7,175,618 | B2 | 2/2007 | Dabney et al. |
| 7,175,621 | B2 | 2/2007 | Heim et al. |
| 7,184,820 | B2 | 2/2007 | Jersey-Willuhn et al. |
| 7,190,933 | B2 | 3/2007 | De Ruijter et al. |
| 7,192,427 | B2 | 3/2007 | Chapelon et al. |
| 7,195,627 | B2 | 3/2007 | Amoah et al. |
| 7,200,010 | B2 | 4/2007 | Broman et al. |
| 7,203,556 | B2 | 4/2007 | Daners |
| 7,204,835 | B2 | 4/2007 | Latterell et al. |
| 7,211,081 | B2 | 5/2007 | Goble |
| 7,214,224 | B2 | 5/2007 | Goble |

(56) References Cited

U.S. PATENT DOCUMENTS

| | | | |
|---|---|---|---|
| 7,217,269 | B2 | 5/2007 | El-Galley et al. |
| 7,220,260 | B2 | 5/2007 | Fleming et al. |
| 7,223,264 | B2 | 5/2007 | Daniel et al. |
| 7,226,447 | B2 | 6/2007 | Uchida et al. |
| 7,229,469 | B1 | 6/2007 | Witzel et al. |
| 7,232,437 | B2 | 6/2007 | Berman et al. |
| 7,233,278 | B2 | 6/2007 | Eriksson |
| 7,238,181 | B2 | 7/2007 | Daners et al. |
| 7,238,183 | B2 | 7/2007 | Kreindel |
| 7,241,296 | B2 | 7/2007 | Buysse et al. |
| 7,244,255 | B2 | 7/2007 | Daners et al. |
| 7,247,155 | B2 | 7/2007 | Hoey et al. |
| 7,250,048 | B2 | 7/2007 | Francischelli et al. |
| 7,250,746 | B2 | 7/2007 | Oswald et al. |
| 7,255,694 | B2 | 8/2007 | Keppel |
| 7,258,688 | B1 | 8/2007 | Shah et al. |
| 7,269,034 | B2 | 9/2007 | Schlecht |
| 7,276,068 | B2 | 10/2007 | Johnson et al. |
| 7,282,048 | B2 | 10/2007 | Goble et al. |
| 7,282,049 | B2 | 10/2007 | Orszulak et al. |
| 7,285,117 | B2 | 10/2007 | Krueger et al. |
| 7,294,127 | B2 | 11/2007 | Leung et al. |
| 7,300,435 | B2 | 11/2007 | Wham et al. |
| 7,300,437 | B2 | 11/2007 | Pozzato |
| 7,303,557 | B2 | 12/2007 | Wham et al. |
| 7,305,311 | B2 | 12/2007 | van Zyl |
| 7,311,703 | B2 | 12/2007 | Turovskiy et al. |
| 7,316,682 | B2 | 1/2008 | Konesky |
| 7,317,954 | B2 | 1/2008 | McGreevy |
| 7,317,955 | B2 | 1/2008 | McGreevy |
| 7,324,357 | B2 | 1/2008 | Miura et al. |
| 7,333,859 | B2 | 2/2008 | Rinaldi et al. |
| 7,341,586 | B2 | 3/2008 | Daniel et al. |
| 7,344,532 | B2 | 3/2008 | Goble et al. |
| 7,353,068 | B2 | 4/2008 | Tanaka et al. |
| 7,354,436 | B2 | 4/2008 | Rioux et al. |
| 7,357,800 | B2 | 4/2008 | Swanson |
| 7,364,577 | B2 | 4/2008 | Wham et al. |
| 7,364,578 | B2 | 4/2008 | Francischelli et al. |
| 7,364,972 | B2 | 4/2008 | Ono et al. |
| 7,367,972 | B2 | 5/2008 | Francischelli et al. |
| RE40,388 | E | 6/2008 | Gines |
| 7,396,336 | B2 | 7/2008 | Orszulak et al. |
| 7,402,754 | B2 | 7/2008 | Kirwan, Jr. et al. |
| D574,323 | S | 8/2008 | Waaler |
| 7,407,502 | B2 | 8/2008 | Strul et al. |
| 7,416,437 | B2 | 8/2008 | Sartor et al. |
| 7,416,549 | B2 | 8/2008 | Young et al. |
| 7,422,582 | B2 | 9/2008 | Malackowski et al. |
| 7,422,586 | B2 | 9/2008 | Morris et al. |
| 7,425,835 | B2 | 9/2008 | Eisele |
| 7,465,302 | B2 | 12/2008 | Odell et al. |
| 7,468,499 | B2 | 12/2008 | Canini et al. |
| 7,470,272 | B2 | 12/2008 | Mulier et al. |
| 7,477,080 | B1 | 1/2009 | Fest |
| 7,479,140 | B2 | 1/2009 | Ellman et al. |
| 7,491,199 | B2 | 2/2009 | Goble |
| 7,491,201 | B2 | 2/2009 | Shields et al. |
| 7,503,917 | B2 | 3/2009 | Sartor et al. |
| 7,511,472 | B1 | 3/2009 | Xia et al. |
| 7,513,896 | B2 | 4/2009 | Orszulak |
| 7,517,351 | B2 | 4/2009 | Culp et al. |
| 7,525,398 | B2 | 4/2009 | Nishimura et al. |
| 7,568,619 | B2 | 8/2009 | Todd et al. |
| 7,573,693 | B2 | 8/2009 | Hornung |
| 7,582,084 | B2 | 9/2009 | Swanson et al. |
| 7,621,041 | B2 | 11/2009 | Banerji et al. |
| 7,628,786 | B2 | 12/2009 | Plaven et al. |
| 7,648,499 | B2 | 1/2010 | Orszulak et al. |
| 7,651,492 | B2 | 1/2010 | Wham |
| 7,651,493 | B2 | 1/2010 | Arts et al. |
| 7,655,003 | B2 | 2/2010 | Lorang et al. |
| 7,666,182 | B2 | 2/2010 | Klett et al. |
| 7,675,429 | B2 | 3/2010 | Cernasov |
| 7,678,105 | B2 | 3/2010 | McGreevy et al. |
| 7,722,601 | B2 | 5/2010 | Wham et al. |
| 7,731,717 | B2 | 6/2010 | Odom et al. |
| 7,736,358 | B2 | 6/2010 | Shores et al. |
| 7,736,359 | B2 | 6/2010 | McPherson |
| 7,744,593 | B2 | 6/2010 | Mihori |
| 7,749,217 | B2 | 7/2010 | Podhajsky |
| 7,766,693 | B2 | 8/2010 | Sartor et al. |
| 7,766,905 | B2 | 8/2010 | Paterson et al. |
| 7,780,662 | B2 | 8/2010 | Bahney |
| 7,780,764 | B2 | 8/2010 | Baksh |
| 7,794,457 | B2 | 9/2010 | McPherson et al. |
| 7,799,020 | B2 | 9/2010 | Shores et al. |
| 7,799,026 | B2 | 9/2010 | Schechter et al. |
| 7,824,400 | B2 | 11/2010 | Keppel |
| 7,834,484 | B2 | 11/2010 | Sartor |
| 7,863,841 | B2 | 1/2011 | Menegoli et al. |
| 7,863,984 | B1 | 1/2011 | Behnke |
| 7,864,129 | B2 | 1/2011 | Konishi |
| 7,879,029 | B2 | 2/2011 | Jimenez |
| 7,879,033 | B2 | 2/2011 | Sartor et al. |
| 7,901,400 | B2 | 3/2011 | Wham et al. |
| 7,927,328 | B2 | 4/2011 | Orszulak et al. |
| 7,947,039 | B2 | 5/2011 | Sartor |
| 7,956,620 | B2 | 6/2011 | Gilbert |
| 7,959,626 | B2 | 6/2011 | Hong et al. |
| 7,972,328 | B2 | 7/2011 | Wham et al. |
| 7,972,332 | B2 | 7/2011 | Arts et al. |
| 7,976,544 | B2 | 7/2011 | McClurken et al. |
| 8,004,121 | B2 | 8/2011 | Sartor |
| 8,012,150 | B2 | 9/2011 | Wham et al. |
| 8,025,660 | B2 | 9/2011 | Plaven et al. |
| 8,034,049 | B2 | 10/2011 | Odom et al. |
| 8,038,676 | B2 | 10/2011 | Fischer |
| 8,070,746 | B2 | 12/2011 | Orton et al. |
| 8,080,008 | B2 | 12/2011 | Wham et al. |
| 8,083,735 | B2 | 12/2011 | Morris |
| 8,096,961 | B2 | 1/2012 | Orszulak et al. |
| 8,104,596 | B2 | 1/2012 | Kim et al. |
| 8,105,323 | B2 | 1/2012 | Buysse et al. |
| 8,113,057 | B2 | 2/2012 | Orszulak et al. |
| 8,133,218 | B2 | 3/2012 | Daw et al. |
| 8,133,222 | B2 | 3/2012 | Ormsby |
| 8,147,485 | B2 | 4/2012 | Wham et al. |
| 8,152,800 | B2 | 4/2012 | Behnke |
| 8,152,801 | B2 | 4/2012 | Goldberg et al. |
| 8,152,802 | B2 | 4/2012 | Podhajsky et al. |
| 8,162,932 | B2 | 4/2012 | Podhajsky et al. |
| 8,167,875 | B2 | 5/2012 | Podhajsky et al. |
| 8,174,267 | B2 | 5/2012 | Brannan et al. |
| 8,187,262 | B2 | 5/2012 | Orszulak |
| 8,200,317 | B2 | 6/2012 | Baxi et al. |
| 8,202,271 | B2 | 6/2012 | Orszulak |
| 8,211,100 | B2 | 7/2012 | Podhajsky et al. |
| 8,216,219 | B2 | 7/2012 | Desinger et al. |
| 8,216,220 | B2 | 7/2012 | Jensen et al. |
| 8,216,223 | B2 | 7/2012 | Wham et al. |
| 8,226,639 | B2 | 7/2012 | Podhajsky et al. |
| 8,231,553 | B2 | 7/2012 | Joseph et al. |
| 8,231,614 | B2 | 7/2012 | Dunning et al. |
| 8,231,616 | B2 | 7/2012 | McPherson et al. |
| 8,235,917 | B2 | 8/2012 | Joseph et al. |
| 8,241,278 | B2 | 8/2012 | Sartor |
| 8,242,782 | B2 | 8/2012 | Brannan et al. |
| 8,248,075 | B2 | 8/2012 | Brannan et al. |
| 8,257,349 | B2 | 9/2012 | Orszulak |
| 8,257,350 | B2 | 9/2012 | Marion |
| 8,262,652 | B2 | 9/2012 | Podhajsky |
| 8,267,928 | B2 | 9/2012 | Orszulak et al. |
| 8,267,929 | B2 | 9/2012 | Wham et al. |
| 8,287,528 | B2 | 10/2012 | Wham et al. |
| 8,287,529 | B2 | 10/2012 | Orszulak |
| 8,292,883 | B2 | 10/2012 | Kabaya et al. |
| 8,298,223 | B2 | 10/2012 | Wham et al. |
| 8,303,337 | B2 | 11/2012 | Ballard et al. |
| 8,303,580 | B2 | 11/2012 | Wham et al. |
| 8,333,759 | B2 | 12/2012 | Podhajsky |
| 8,346,370 | B2 | 1/2013 | Haley et al. |
| 8,353,903 | B2 | 1/2013 | Podhajsky |
| 8,353,905 | B2 | 1/2013 | Jensen et al. |

(56) References Cited

U.S. PATENT DOCUMENTS

| | | | |
|---|---|---|---|
| 8,377,053 | B2 | 2/2013 | Orszulak |
| 8,377,054 | B2 | 2/2013 | Gilbert |
| 8,382,751 | B2 | 2/2013 | Gilbert et al. |
| 8,398,627 | B2 | 3/2013 | Hosier |
| 8,403,924 | B2 | 3/2013 | Behnke et al. |
| 8,409,186 | B2 | 4/2013 | Behnke et al. |
| 8,454,590 | B2 | 6/2013 | Smith |
| 8,460,284 | B2 | 6/2013 | Aronow et al. |
| 8,469,956 | B2 | 6/2013 | McKenna et al. |
| 8,475,447 | B2 | 7/2013 | Orszulak et al. |
| 8,485,993 | B2 | 7/2013 | Orszulak et al. |
| 8,486,061 | B2 | 7/2013 | Podhajsky |
| 8,512,232 | B2 | 8/2013 | Rothberg et al. |
| 8,523,855 | B2 | 9/2013 | Keppel |
| 8,540,709 | B2 | 9/2013 | Allen |
| 8,542,019 | B2 | 9/2013 | Brannan et al. |
| 8,784,418 | B2 | 7/2014 | Romero |
| 9,226,767 | B2 | 1/2016 | Stulen et al. |
| 9,332,987 | B2 | 5/2016 | Leimbach et al. |
| 9,861,425 | B2 | 1/2018 | Behnke |
| 10,406,690 | B1 | 9/2019 | Blankespoor et al. |
| 10,573,713 | B2 | 2/2020 | Wen |
| 10,653,417 | B2 | 5/2020 | Shelton, IV et al. |
| 10,761,524 | B2 | 9/2020 | Wallace |
| 11,242,458 | B2 | 2/2022 | Takada et al. |
| 11,278,346 | B2 | 3/2022 | Messerly et al. |
| 2002/0022836 | A1 | 2/2002 | Goble et al. |
| 2002/0029036 | A1 | 3/2002 | Goble et al. |
| 2003/0153908 | A1 | 8/2003 | Goble et al. |
| 2003/0181898 | A1 | 9/2003 | Bowers |
| 2003/0229344 | A1 | 12/2003 | Dycus et al. |
| 2004/0015159 | A1 | 1/2004 | Slater et al. |
| 2004/0030330 | A1 | 2/2004 | Brassell et al. |
| 2004/0068304 | A1 | 4/2004 | Paton et al. |
| 2004/0097912 | A1 | 5/2004 | Gonnering |
| 2004/0133189 | A1 | 7/2004 | Sakurai |
| 2004/0172016 | A1 | 9/2004 | Bek et al. |
| 2004/0193021 | A1 | 9/2004 | Zdeblick et al. |
| 2005/0004634 | A1 | 1/2005 | Ricart et al. |
| 2005/0021020 | A1 | 1/2005 | Blaha |
| 2005/0109111 | A1 | 5/2005 | Manlove et al. |
| 2005/0109935 | A1 | 5/2005 | Manlove et al. |
| 2005/0131390 | A1 | 6/2005 | Heinrich et al. |
| 2006/0079774 | A1 | 4/2006 | Anderson |
| 2006/0111711 | A1 | 5/2006 | Goble |
| 2006/0155270 | A1 | 7/2006 | Hancock |
| 2006/0161148 | A1 | 7/2006 | Behnke |
| 2006/0191926 | A1 | 8/2006 | Ray et al. |
| 2006/0224053 | A1 | 10/2006 | Black et al. |
| 2006/0224152 | A1 | 10/2006 | Behnke et al. |
| 2006/0291178 | A1 | 12/2006 | Shih |
| 2007/0088413 | A1 | 4/2007 | Weber et al. |
| 2007/0093801 | A1 | 4/2007 | Behnke |
| 2007/0173802 | A1 | 7/2007 | Keppel |
| 2007/0173803 | A1 | 7/2007 | Wham et al. |
| 2007/0173805 | A1 | 7/2007 | Weinberg et al. |
| 2007/0173811 | A1 | 7/2007 | Couture et al. |
| 2007/0173813 | A1 | 7/2007 | Odom |
| 2007/0203481 | A1 | 8/2007 | Gregg et al. |
| 2007/0265612 | A1 | 11/2007 | Behnke et al. |
| 2007/0282320 | A1 | 12/2007 | Buysse et al. |
| 2008/0004619 | A1 | 1/2008 | Malis et al. |
| 2008/0015563 | A1 | 1/2008 | Hoey et al. |
| 2008/0015570 | A1 | 1/2008 | Ormsby et al. |
| 2008/0071257 | A1 | 3/2008 | Kotmel et al. |
| 2008/0071260 | A1 | 3/2008 | Shores |
| 2008/0132893 | A1 | 6/2008 | D'Amelio et al. |
| 2008/0147056 | A1 | 6/2008 | van der Weide et al. |
| 2008/0177199 | A1 | 7/2008 | Podhajsky |
| 2008/0203997 | A1 | 8/2008 | Foran et al. |
| 2008/0234574 | A1 | 9/2008 | Hancock et al. |
| 2008/0262489 | A1 | 10/2008 | Steinke |
| 2008/0281311 | A1 | 11/2008 | Dunning et al. |
| 2008/0281315 | A1 | 11/2008 | Gines |
| 2008/0281316 | A1 | 11/2008 | Carlton et al. |
| 2008/0287943 | A1 | 11/2008 | Weber et al. |
| 2008/0319350 | A1 | 12/2008 | Wallace et al. |
| 2008/0319442 | A1 | 12/2008 | Unger et al. |
| 2009/0018536 | A1 | 1/2009 | Behnke |
| 2009/0030477 | A1 | 1/2009 | Jarrard |
| 2009/0082765 | A1 | 3/2009 | Collins et al. |
| 2009/0146635 | A1 | 6/2009 | Qiu et al. |
| 2009/0157071 | A1 | 6/2009 | Wham et al. |
| 2009/0234350 | A1 | 9/2009 | Behnke et al. |
| 2009/0240244 | A1 | 9/2009 | Malis et al. |
| 2009/0248003 | A1 | 10/2009 | Orszulak |
| 2009/0248006 | A1 | 10/2009 | Paulus et al. |
| 2009/0248007 | A1 | 10/2009 | Falkenstein et al. |
| 2009/0254077 | A1 | 10/2009 | Craig |
| 2009/0259224 | A1 | 10/2009 | Wham et al. |
| 2009/0292283 | A1 | 11/2009 | Odom |
| 2010/0030210 | A1 | 2/2010 | Paulus |
| 2010/0042093 | A9 | 2/2010 | Wham et al. |
| 2010/0057076 | A1 | 3/2010 | Behnke et al. |
| 2010/0063494 | A1 | 3/2010 | Orszulak |
| 2010/0063497 | A1 | 3/2010 | Orszulak |
| 2010/0076424 | A1 | 3/2010 | Carr |
| 2010/0082022 | A1 | 4/2010 | Haley et al. |
| 2010/0082023 | A1 | 4/2010 | Brannan et al. |
| 2010/0082083 | A1 | 4/2010 | Brannan et al. |
| 2010/0082084 | A1 | 4/2010 | Brannan et al. |
| 2010/0094271 | A1 | 4/2010 | Ward et al. |
| 2010/0094275 | A1 | 4/2010 | Wham |
| 2010/0094288 | A1 | 4/2010 | Kerr |
| 2010/0114090 | A1 | 5/2010 | Hosier |
| 2010/0168572 | A1 | 7/2010 | Sliwa et al. |
| 2010/0168730 | A1 | 7/2010 | Hancock et al. |
| 2010/0168741 | A1 | 7/2010 | Sanai et al. |
| 2010/0179533 | A1 | 7/2010 | Podhajsky |
| 2010/0191233 | A1 | 7/2010 | Wham et al. |
| 2010/0211063 | A1 | 8/2010 | Wham et al. |
| 2010/0217258 | A1 | 8/2010 | Floume et al. |
| 2010/0217264 | A1 | 8/2010 | Odom et al. |
| 2010/0268220 | A1 | 10/2010 | Johnson et al. |
| 2010/0318080 | A1 | 12/2010 | Keppel |
| 2011/0028963 | A1 | 2/2011 | Gilbert |
| 2011/0054460 | A1 | 3/2011 | Gilbert |
| 2011/0060329 | A1 | 3/2011 | Gilbert et al. |
| 2011/0071516 | A1 | 3/2011 | Gregg |
| 2011/0071521 | A1 | 3/2011 | Gilbert |
| 2011/0077631 | A1 | 3/2011 | Keller |
| 2011/0077639 | A1 | 3/2011 | Brannan et al. |
| 2011/0087213 | A1 | 4/2011 | Messerly et al. |
| 2011/0112530 | A1 | 5/2011 | Keller |
| 2011/0115562 | A1 | 5/2011 | Gilbert |
| 2011/0144635 | A1 | 6/2011 | Harper et al. |
| 2011/0178516 | A1 | 7/2011 | Orszulak et al. |
| 2011/0204903 | A1 | 8/2011 | Gilbert |
| 2011/0208179 | A1 | 8/2011 | Prakash et al. |
| 2011/0213354 | A1 | 9/2011 | Smith |
| 2011/0213355 | A1 | 9/2011 | Behnke, II |
| 2011/0301607 | A1 | 12/2011 | Couture |
| 2011/0318948 | A1 | 12/2011 | Plaven et al. |
| 2011/0319881 | A1 | 12/2011 | Johnston |
| 2012/0004703 | A1 | 1/2012 | Deborski et al. |
| 2012/0010610 | A1 | 1/2012 | Keppel |
| 2012/0022521 | A1 | 1/2012 | Odom et al. |
| 2012/0028373 | A1 | 2/2012 | Belen et al. |
| 2012/0029515 | A1 | 2/2012 | Couture |
| 2012/0089139 | A1 | 4/2012 | Wham et al. |
| 2012/0101491 | A1 | 4/2012 | Blaha |
| 2012/0116268 | A1 | 5/2012 | Orszulak et al. |
| 2012/0123405 | A1 | 5/2012 | Moua et al. |
| 2012/0130256 | A1 | 5/2012 | Buysse et al. |
| 2012/0150170 | A1 | 6/2012 | Buysse et al. |
| 2012/0172866 | A1 | 7/2012 | Behnke, II |
| 2012/0179156 | A1 | 7/2012 | Behnke, II |
| 2012/0220997 | A1 | 8/2012 | Johnston |
| 2012/0239020 | A1 | 9/2012 | Cunningham |
| 2012/0239025 | A1 | 9/2012 | Smith |
| 2012/0239026 | A1 | 9/2012 | Orszulak et al. |
| 2012/0265194 | A1 | 10/2012 | Podhajsky |
| 2012/0265195 | A1 | 10/2012 | Gilbert |
| 2012/0265196 | A1 | 10/2012 | Turner et al. |

(56) References Cited

U.S. PATENT DOCUMENTS

| 2012/0303017 A1 | 11/2012 | Brannan et al. |
| 2012/0310241 A1 | 12/2012 | Orszulak |
| 2012/0316555 A1 | 12/2012 | Orszulak et al. |
| 2012/0316556 A1 | 12/2012 | Podhajsky |
| 2013/0006235 A1 | 1/2013 | Podhajsky et al. |
| 2013/0023867 A1 | 1/2013 | Collins |
| 2013/0023869 A1 | 1/2013 | Orszulak |
| 2013/0023870 A1 | 1/2013 | Collins |
| 2013/0023871 A1 | 1/2013 | Collins |
| 2013/0030432 A1 | 1/2013 | Garrison et al. |
| 2013/0035679 A1 | 2/2013 | Orszulak |
| 2013/0041364 A1 | 2/2013 | Orszulak |
| 2013/0041367 A1 | 2/2013 | Wham et al. |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079763 A1 | 3/2013 | Heckel et al. |
| 2013/0158541 A1 | 6/2013 | Orszulak |
| 2013/0178848 A1 | 7/2013 | Gilbert et al. |
| 2013/0184698 A1 | 7/2013 | Behnke, II et al. |
| 2013/0184699 A1 | 7/2013 | Behnke, II et al. |
| 2013/0190750 A1 | 7/2013 | Behnke, II et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |
| 2014/0025064 A1 | 1/2014 | Collins et al. |
| 2014/0148803 A1* | 5/2014 | Taylor ................. A61B 18/1445 606/49 |
| 2014/0163431 A1 | 6/2014 | Orszulak et al. |
| 2015/0088117 A1* | 3/2015 | Gilbert ............... A61B 18/1206 606/34 |
| 2015/0297286 A1* | 10/2015 | Boudreaux ........ A61B 18/1445 606/51 |
| 2016/0120601 A1 | 5/2016 | Boudreaux et al. |
| 2016/0175031 A1 | 6/2016 | Boudreaux |
| 2017/0189095 A1* | 7/2017 | Danziger ........... A61B 18/1206 |
| 2020/0106220 A1* | 4/2020 | Henderson .......... H01R 13/703 |
| 2020/0107845 A1* | 4/2020 | Kabala ............. A61B 17/22031 |
| 2020/0397432 A1 | 12/2020 | Messerly et al. |
| 2021/0236198 A1 | 8/2021 | Boudreaux |
| 2023/0108257 A1 | 4/2023 | Puterbaugh et al. |

FOREIGN PATENT DOCUMENTS

| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0309942 A2 | 4/1989 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0503200 A2 | 9/1992 |
| EP | 0556705 A1 | 8/1993 |
| EP | 0569130 A1 | 11/1993 |
| EP | 0608609 A2 | 8/1994 |
| EP | 0617925 A1 | 10/1994 |
| EP | 0694291 A1 | 1/1996 |
| EP | 0836868 A2 | 4/1998 |
| EP | 0870473 A2 | 10/1998 |
| EP | 0878169 A1 | 11/1998 |
| EP | 0880220 A2 | 11/1998 |
| EP | 0882955 A1 | 12/1998 |
| EP | 0640317 B1 | 9/1999 |
| EP | 1051948 A2 | 11/2000 |
| EP | 1053720 A1 | 11/2000 |
| EP | 1146827 A1 | 10/2001 |
| EP | 1151725 A1 | 11/2001 |
| EP | 1157667 A2 | 11/2001 |
| EP | 1263181 A1 | 12/2002 |
| EP | 1278007 | 1/2003 |
| EP | 1293171 A2 | 3/2003 |
| EP | 1366724 A1 | 12/2003 |
| EP | 1472984 A1 | 11/2004 |
| EP | 1495712 A1 | 1/2005 |
| EP | 1500378 A1 | 1/2005 |
| EP | 1535581 A2 | 6/2005 |
| EP | 1594392 A2 | 11/2005 |
| EP | 1609430 A1 | 12/2005 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 A1 | 4/2007 |
| EP | 1810628 A1 | 7/2007 |
| EP | 1810630 A1 | 7/2007 |
| EP | 1810631 A2 | 7/2007 |
| EP | 1810632 A1 | 7/2007 |
| EP | 1810633 A2 | 7/2007 |
| EP | 1810634 A1 | 7/2007 |
| EP | 1849425 A1 | 10/2007 |
| EP | 1854423 A2 | 11/2007 |
| EP | 1862137 A1 | 12/2007 |
| EP | 1902681 A1 | 3/2008 |
| EP | 1994904 | 11/2008 |
| EP | 2025297 A2 | 2/2009 |
| EP | 2042116 A1 | 4/2009 |
| EP | 2100566 A1 | 9/2009 |
| EP | 2111812 A2 | 10/2009 |
| EP | 2156800 A1 | 2/2010 |
| EP | 2253286 A1 | 11/2010 |
| EP | 2301463 A1 | 3/2011 |
| EP | 2345454 A1 | 7/2011 |
| EP | 3824828 | 11/2014 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |

(56) References Cited

FOREIGN PATENT DOCUMENTS

| | | | |
|----|------------|-----|---------|
| GB | 607850 | A | 9/1948 |
| GB | 702510 | A | 1/1954 |
| GB | 855459 | A | 11/1960 |
| GB | 902775 | A | 8/1962 |
| GB | 1290304 | A | 9/1972 |
| GB | 2154881 | A | 9/1985 |
| GB | 2164473 | A | 3/1986 |
| GB | 2214430 | A | 9/1989 |
| GB | 2331247 | A | 5/1999 |
| GB | 2358934 | A | 8/2001 |
| GB | 2434872 | A | 8/2007 |
| GB | 2559373 | | 2/2017 |
| JP | 63005876 | | 1/1988 |
| JP | 2002065690 | A | 3/2002 |
| JP | 2005185657 | A | 7/2005 |
| SU | 166452 | | 11/1964 |
| SU | 727201 | A2 | 4/1980 |
| WO | 9206642 | | 4/1992 |
| WO | 9207622 | A1 | 5/1992 |
| WO | 9320747 | A1 | 10/1993 |
| WO | 9324066 | A1 | 12/1993 |
| WO | 9410922 | A1 | 5/1994 |
| WO | 9424949 | A1 | 11/1994 |
| WO | 9428809 | A1 | 12/1994 |
| WO | 9509577 | A1 | 4/1995 |
| WO | 9518575 | A1 | 7/1995 |
| WO | 9519148 | A1 | 7/1995 |
| WO | 95/25472 | A1 | 9/1995 |
| WO | 9525471 | A2 | 9/1995 |
| WO | 9602180 | A2 | 2/1996 |
| WO | 9604860 | A1 | 2/1996 |
| WO | 9608794 | A1 | 3/1996 |
| WO | 9618349 | A2 | 6/1996 |
| WO | 9629946 | A1 | 10/1996 |
| WO | 96/39088 | A1 | 12/1996 |
| WO | 9639085 | A1 | 12/1996 |
| WO | 9639086 | A1 | 12/1996 |
| WO | 9639914 | A1 | 12/1996 |
| WO | 9706739 | A2 | 2/1997 |
| WO | 9706740 | A2 | 2/1997 |
| WO | 9706855 | A2 | 2/1997 |
| WO | 9710763 | A1 | 3/1997 |
| WO | 9711648 | A2 | 4/1997 |
| WO | 9717029 | A1 | 5/1997 |
| WO | 97/43971 | A2 | 11/1997 |
| WO | 9807378 | A1 | 2/1998 |
| WO | 9818395 | A1 | 5/1998 |
| WO | 9827880 | | 7/1998 |
| WO | 9912607 | A1 | 3/1999 |
| WO | 9956647 | A1 | 11/1999 |
| WO | 00/48672 | A1 | 8/2000 |
| WO | 0054683 | A1 | 9/2000 |
| WO | 0101847 | | 1/2001 |
| WO | 0200129 | | 1/2002 |
| WO | 0211634 | | 2/2002 |
| WO | 0232333 | | 4/2002 |
| WO | 0232335 | | 4/2002 |
| WO | 0245589 | A2 | 6/2002 |
| WO | 0247565 | | 6/2002 |
| WO | 02053048 | A1 | 7/2002 |
| WO | 02088128 | A1 | 11/2002 |
| WO | 03047446 | A1 | 6/2003 |
| WO | 03090635 | A1 | 11/2003 |
| WO | 03092520 | A1 | 11/2003 |
| WO | 03090630 | A3 | 4/2004 |
| WO | 2004028385 | A1 | 4/2004 |
| WO | 2004043240 | A2 | 5/2004 |
| WO | 2004047659 | A2 | 6/2004 |
| WO | 2004052182 | A2 | 6/2004 |
| WO | 2004073488 | | 9/2004 |
| WO | 2004098385 | A2 | 11/2004 |
| WO | 2004103156 | | 12/2004 |
| WO | 2005046496 | A1 | 5/2005 |
| WO | 2005048809 | | 6/2005 |
| WO | 2005050151 | | 6/2005 |
| WO | 2005060365 | A2 | 7/2005 |
| WO | 2005060849 | A1 | 7/2005 |
| WO | 2005115235 | A1 | 12/2005 |
| WO | 2005117735 | A1 | 12/2005 |
| WO | 2006050888 | A1 | 5/2006 |
| WO | 2006105121 | A2 | 10/2006 |
| WO | 2007055491 | A1 | 5/2007 |
| WO | 2007067522 | A2 | 6/2007 |
| WO | 2007076924 | A2 | 7/2007 |
| WO | 2007105963 | A1 | 9/2007 |
| WO | 2008002517 | A1 | 1/2008 |
| WO | 2008003058 | A2 | 1/2008 |
| WO | 2008011575 | A1 | 1/2008 |
| WO | 2008043999 | A2 | 4/2008 |
| WO | 2008044000 | A1 | 4/2008 |
| WO | 2008044013 | A2 | 4/2008 |
| WO | 2008053532 | A1 | 5/2008 |
| WO | 2008070562 | A1 | 6/2008 |
| WO | 2008071914 | A2 | 6/2008 |
| WO | 2008101356 | A1 | 8/2008 |
| WO | 2008110756 | A2 | 9/2008 |
| WO | 2010129348 | A1 | 11/2010 |
| WO | 2017058617 | | 9/2016 |
| WO | 2020051450 | A1 | 3/2020 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation—'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

U.S. Appl. No. 10/406,690 dated Apr. 3, 2003 inventor: Behnke.

U.S. Appl. No. 10/573,713 dated Mar. 28, 2006 inventor: Wham.

U.S. Appl. No. 10/761,524 dated Jan. 21, 2004 inventor: Wham.

U.S. Appl. No. 11/242,458 dated Oct. 3, 2005 inventor: Becker.

U.S. Appl. No. 14/096,341 dated Dec. 4, 2013 inventor: Johnson.

U.S. Appl. No. 14/098,859 dated Dec. 6, 2013 inventor: Johnson.

U.S. Appl. No. 14/100,113 dated Dec. 9, 2013 inventor: Gilbert.

U.S. Appl. No. 14/147,294 dated Jan. 3, 2014 inventor: Gilbert.

U.S. Appl. No. 14/147,312 dated Jan. 3, 2014 inventor: Gilbert.

U.S. Appl. No. 14/168,296 dated Jan. 30, 2014, inventor: Mattmiller.

U.S. Appl. No. 14/174,551 dated Feb. 6, 2014 inventor: Johnson.

U.S. Appl. No. 14/174,607 dated Feb. 6, 2014 inventor: Friedrichs.

U.S. Appl. No. 14/179,724 dated Feb. 13, 2014 inventor: Johnson.

U.S. Appl. No. 14/180,965 dated Feb. 14, 2014 inventor: Larson.

U.S. Appl. No. 14/181,114 dated Feb. 14, 2014 inventor: Larson.

U.S. Appl. No. 14/182,797 dated Feb. 18, 2014 inventor: Wham.

U.S. Appl. No. 14/190,830 dated Feb. 26, 2014 inventor: Johnson.

U.S. Appl. No. 14/190,895 dated Feb. 26, 2014 inventor: Gilbert.

U.S. Appl. No. 14/255,051 dated Apr. 17, 2014 inventor: Coulson.

U.S. Appl. No. 14/262,219 dated Apr. 25, 2014, inventor: Gilbert.

U.S. Appl. No. 14/267,066 dated May 1, 2014, inventor: Friedrichs.

U.S. Appl. No. 14/268,187 dated May 2, 2014, inventor: Kerr.

U.S. Appl. No. 14/283,604 dated May 21, 2014, inventor: Behnke.

U.S. Appl. No. 14/297,771 dated Jun. 6, 2014, inventor: Wham.

Extended European Search Report issued in corresponding application EP 22177409.4 dated Nov. 3, 2022 (8 pages).

U.S. Appl. No. 14/297,812 dated Jun. 6, 2014, inventor: Wham.

U.S. Appl. No. 14/297,890 dated Jun. 6, 2014, inventor: Wham.

U.S. Appl. No. 14/320,762 dated Jul. 1, 2014, inventor: Gilbert.

U.S. Appl. No. 14/320,804 dated Jul. 1, 2014, inventor: Gilbert.

Extended EP Search Report for application No. 22196234.3 dated Jun. 15, 2023 (14 pages).

Partial European Search Report dated Feb. 10, 2023 corresponding to counterpart Patent Application EP 2196234.3 (14 pages).

* cited by examiner

| 0=switch Open | | | |
|---|---|---|---|
| 1=switch Closed | | | |
| | | | |
| Switch | | | |
| Activation | Jaw aperture | Lever | Instrument State |
| 0 | 0 | 0 | Activation off |
| 0 | 0 | 1 | Activation off |
| 0 | 1 | 0 | Activation off |
| 0 | 1 | 1 | Activation off |
| 1 | 0 | 0 | Activation on. jaw and lever open |
| 1 | 0 | 1 | Activation on. jaw open and lever closed |
| 1 | 1 | 0 | Activation on. jaw closed and lever open |
| 1 | 1 | 1 | Activation on. jaw and lever closed |

MULTIPLEXED HAND SWITCHES FOR USE WITH ELECTROSURGICAL GENERATORS

CROSS-REFERENCE TO RELATED APPLICATION

The present application claims the benefit of and priority to U.S. Provisional Application No. 63/197,534, filed on Jun. 7, 2021. The entire disclosure of the foregoing application is incorporated by reference herein.

BACKGROUND

Technical Field

The present disclosure relates to systems and methods for controlling an electrosurgical generator. In particular, the present disclosure relates to controlling an electrosurgical generator using multiplexed switches disposed in an electrosurgical device, such that each of the switches is actuated by a corresponding movable component of the electrosurgical device providing the status of the components to the electrosurgical generator, which may then control output based on the status of the switches.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Hand switches are currently used with monopolar electrosurgical pencils. Thus, there is a need to provide similar hand switch functionality in other electrosurgical devices, such as bipolar forceps.

SUMMARY

According to one embodiment of the present disclosure, an electrosurgical system is disclosed. The electrosurgical system includes an electrosurgical device having: a main switch, a button configured to actuate the main switch, at least one secondary switch, and a movable component configured to actuate the second switch. The system also includes an electrosurgical generator coupled to the electrosurgical device, the electrosurgical generator is configured to generate an electrosurgical output in response to actuation of the main switch and the at least one secondary switch.

Implementations of the above embodiment may include one or more of the following features. According to one aspect of the above embodiment, the electrosurgical device may include a pair of opposing jaw members movable between an open jaw position and a closed jaw position. The secondary switch may be disposed on one jaw member of the pair of opposing jaw members and is actuated when the pair of opposing jaw members are in the closed jaw position. The electrosurgical device may include a lever that is movable between an open lever position and a closed lever position to move the pair of opposing jaw members between the open jaw position and the closed jaw position, respectively. The electrosurgical device may include a handle and the secondary switch may be disposed on the handle and is actuated by the lever being in the closed lever position. The electrosurgical device may further include a multiplexer circuit configured to output a voltage signal based on actuation of the main switch and the at least one secondary switch. The electrosurgical generator may include a signal processor coupled to the multiplexer circuit, the signal processor configured to output an activation signal based on the voltage signal. The signal processor may be a voltage comparator or an analog-to-digital converter coupled to a digital processor. The electrosurgical generator may further include a controller coupled to signal processor, the controller may be configured to output a control signal in response to the activation signal. The electrosurgical generator may further include: a power supply configured to output a direct current; a radio frequency inverter coupled to the power supply and configured to generate the electrosurgical output by inverting the direct current. The controller may be further configured to output the control signal to the radio frequency inverter to generate the electrosurgical output.

According to another embodiment of the present disclosure, an electrosurgical system is disclosed. The electrosurgical system includes an electrosurgical device having: a first switch and a button configured to actuate the first switch. The electrosurgical device also includes a second switch and a pair of opposing jaw members movable between an open jaw position and a closed jaw position, where the second switch is actuated when the pair of opposing jaw members are in the closed jaw position. The electrosurgical device further includes a third switch and a lever movable between an open lever position and a closed lever position to move the pair of opposing jaw members between the open jaw position and the closed jaw position, respectively, such that the lever actuates the third switch in the closed lever position.

Implementations of the above embodiment may include one or more of the following features. According to one aspect of the above embodiment, the electrosurgical system further includes an electrosurgical generator coupled to the electrosurgical device. The electrosurgical generator is configured to generate an electrosurgical output in response to actuation of the first switch, the second switch, and the third switch. The electrosurgical device may further include a multiplexer circuit configured to output a voltage signal based on actuation of the first switch, the second switch, and the third switch. The electrosurgical generator may include a signal processor coupled to the multiplexer circuit, the signal processor configured to output an activation signal based on the voltage signal. The electrosurgical generator may further include a controller coupled to signal processor, the controller is configured to output a control signal in response to the activation signal.

According to a further embodiment of the present disclosure, a method for controlling an electrosurgical generator is disclosed. The method includes actuating a lever between an open lever position and a closed lever position to move a pair of opposing jaw members between an open jaw position and a closed jaw position. The method also includes activating a jaw switch when the pair of opposing jaw members are in the closed jaw position; activating a lever switch when the lever is in the closed lever position; activating a main switch by pressing a button; determining a type of output to be generated by the electrosurgical generator based on activation of the lever switch and the jaw switch; and activating an electrosurgical generator to output the determined output in response to activation of the main switch Implementations of the above embodiment may include one or more of the following features. According to one aspect of the above embodiment, the method may further include determining whether each of the jaw switch, the lever switch, and the main switch is activated based on a voltage signal output by a multiplexer circuit. The method may further include determining whether each of the jaw switch, the lever switch, and the main switch is activated based on a voltage signal output by a multiplexer circuit.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
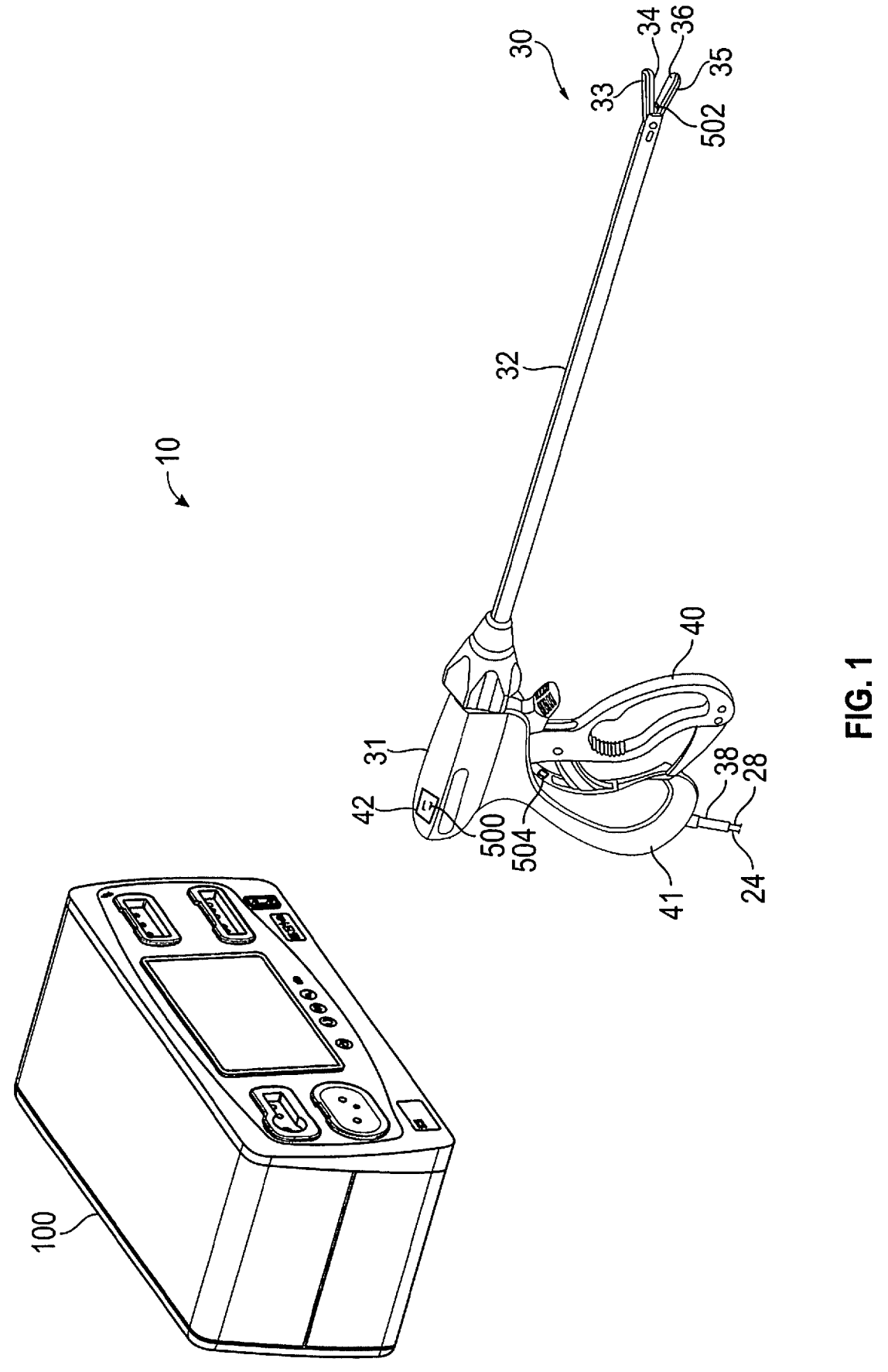
FIG. 1 is a perspective view of an electrosurgical system according to an embodiment of the present disclosure.

Embodiments of the presently disclosed system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Figure 3:
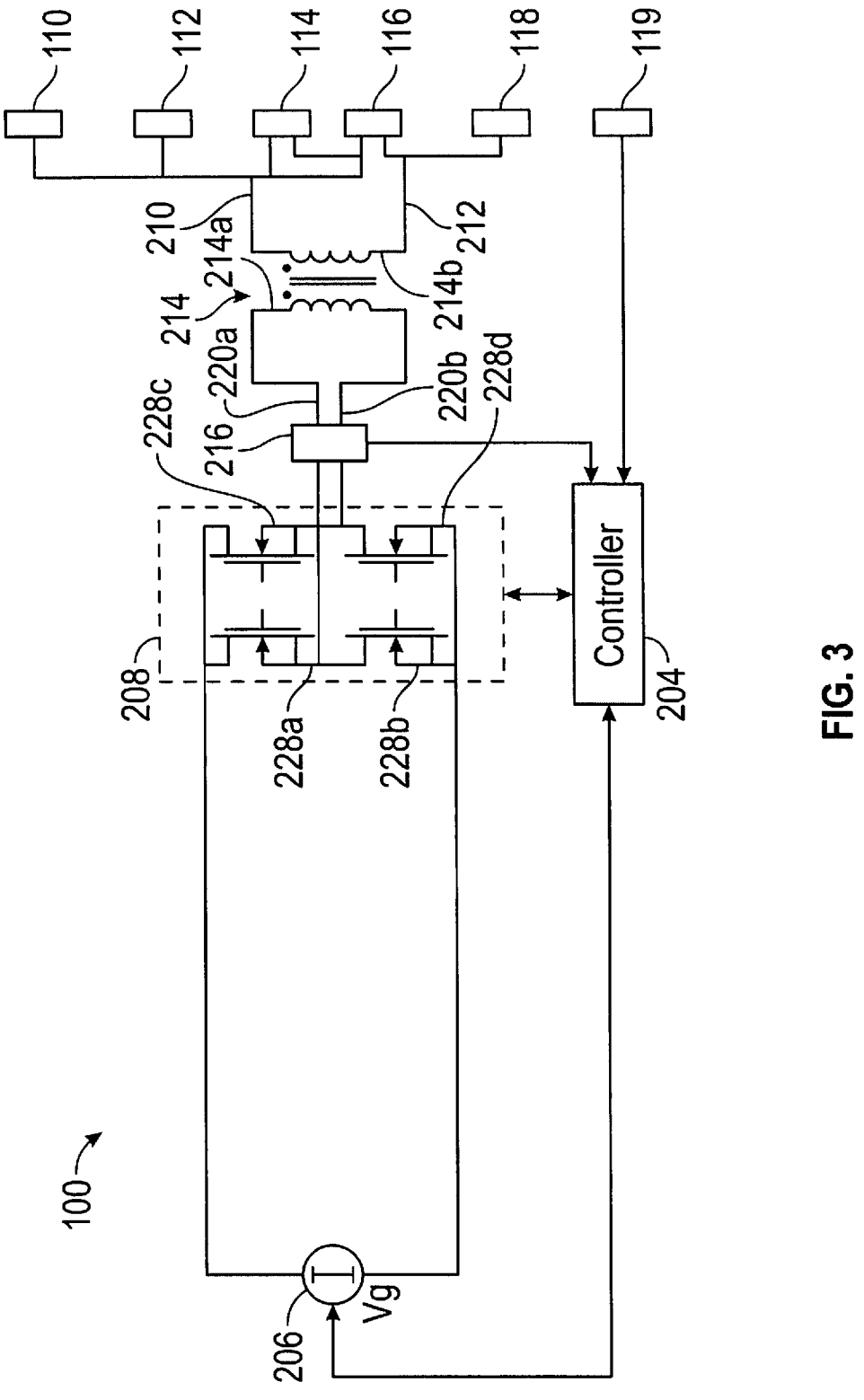
FIG. 3 is a schematic diagram of the electrosurgical generator of FIG. 1 according to an embodiment of the present disclosure.

Referring to FIG. 1 an electrosurgical system 10 is shown which includes one or more a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 100 through cable 38 that includes the supply and return lines 24, 28, which may be coupled to the active and return terminals 210 and 212, respectively (FIG. 3). The electrosurgical forceps 30 is coupled to the generator 100 at a port having connections to the active and return terminals 210 and 212 (e.g., pins) via a plug disposed at the end of the cable 38, wherein the plug includes contacts from the supply and return lines 24, 28 as described in more detail below. The forceps 30 also includes a button 42 configured to signal to the generator 100 to output electrosurgical energy through the electrodes 34 and 36.

The forceps 30 also includes a lever 40 movable relative to a handle 41. The handle 41 is formed as part of the housing 31 and the lever 40 may be pivotably coupled within the housing 31. The lever 40 actuates, i.e., opens and closes, the jaw members 33 and 35, via one or more mechanical linkages. U.S. Pat. No. 8,784,418, titled "Endoscopic surgical forceps", provides additional disclosure of a bipolar electrosurgical forceps, the entire disclosure of which is incorporated by reference here. The lever 40 is movable from an open position (i.e., furthest distance from the handle 41) to a closed position (i.e., closest distance from the handle 41). The movement of the jaw members 33 and 35 corresponds to the movement of the lever 40. Thus, the jaw members are movable from an open position (i.e., furthest distance between the jaw members 33 and 35) to a closed position (i.e., closest between the jaw members 33 and 35, clamping tissue).

Figure 2:
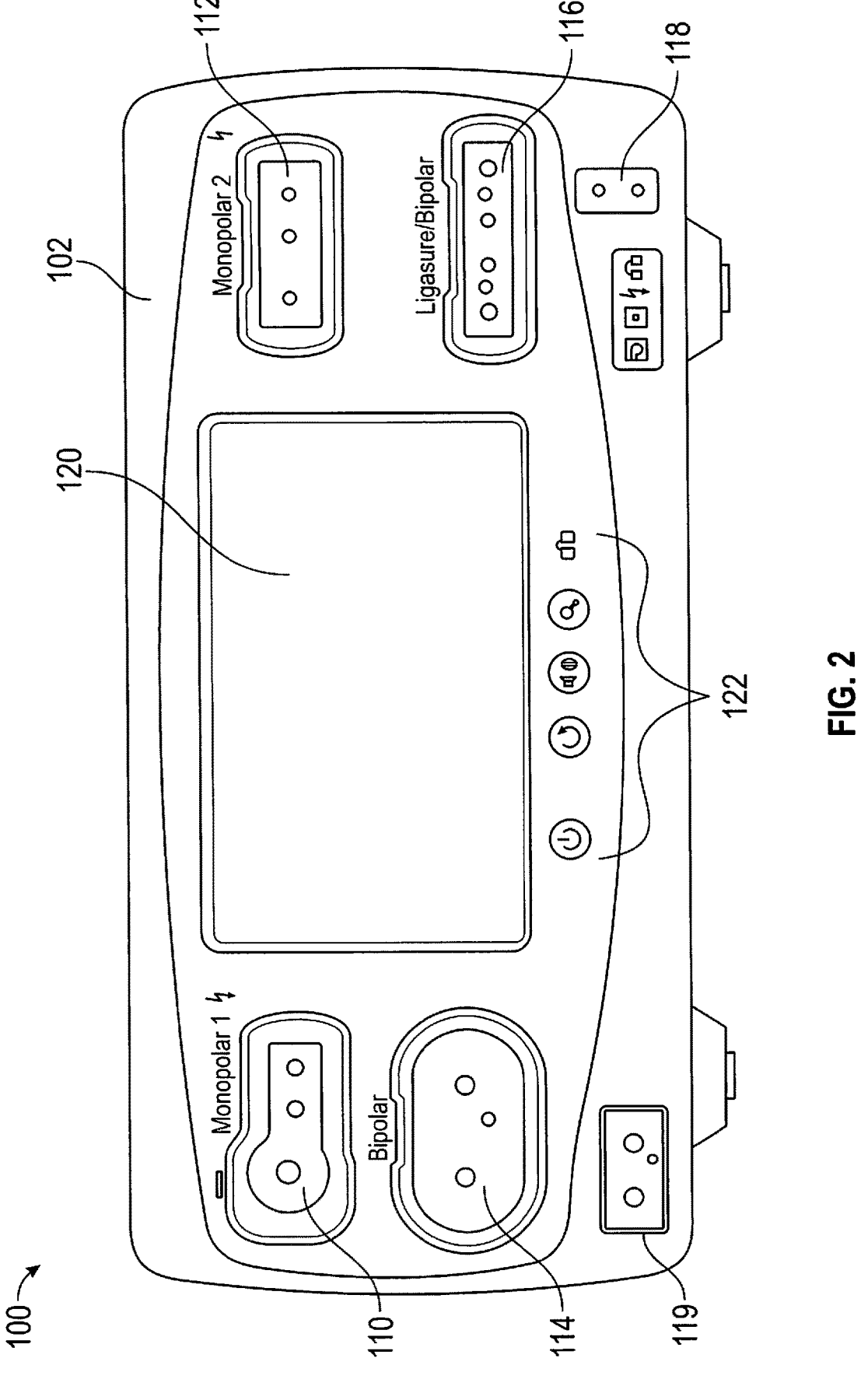
FIG. 2 is a front view of an electrosurgical generator of FIG. 1 according to an embodiment of the present disclosure.

With reference to FIG. 2, a front face 102 of the generator 100 is shown. The generator 100 may include a plurality of ports 110, 112, 114, 116 to accommodate various types of electrosurgical instruments and a port 118 for coupling to a return electrode pad and a port 119 configured to couple to a footswitch. The ports 110 and 112 are configured to couple to the monopolar electrosurgical instruments (e.g., first electrosurgical instrument 12). The ports 114 and 116 are configured to couple to bipolar electrosurgical instruments (e.g., second electrosurgical instrument 14). The generator 100 includes a display 120 for providing the user with variety of output information (e.g., intensity settings, treatment complete indicators, etc.). The display 120 is a touchscreen configured to display a menu corresponding to each of the ports 110, 112, 114, 116 and the instrument coupled. The user also adjusts inputs by touching corresponding menu options. The generator 100 also includes suitable input controls 122 (e.g., buttons, activators, switches, touch screen, etc.) for controlling the generator 100.

The generator 100 is configured to operate in a variety of modes and is configured to output monopolar and/or bipolar waveforms corresponding to the selected mode. Each of the modes may be activated by the button 42 disposed on the forceps 30. Each of the modes operates based on a prepro- grammed power curve that limits how much power is output by the generator 100 at varying impedance ranges of the load (e.g., tissue). Each of the power curves includes power, voltage and current control ranges that are defined by the user-selected intensity setting and the measured minimum impedance of the load.

The generator 100 may operate in the following monopo- lar modes, which include, but are not limited to, cut, blend, division with hemostasis, fulgurate and spray. The generator 100 may operate in the following bipolar modes, including bipolar cutting, bipolar coagulation, automatic bipolar which operates in response to sensing tissue contact, and various algorithm-controlled vessel sealing modes. The gen- erator 100 may be configured to deliver energy required to power an ultrasonic transducer. Thereby enabling control and modulation of ultrasonic surgical instruments.

Each of the RF waveforms may be either monopolar or bipolar RF waveforms, each of which may be continuous or discontinuous and may have a carrier frequency from about 200 kHz to about 500 kHz. As used herein, continuous waveforms are waveforms that have a 100% duty cycle. In embodiments, continuous waveforms are used to impart a cutting effect on tissue. Conversely, discontinuous wave- forms are waveforms that have a non-continuous duty cycle, e.g., below 100%. In embodiments, discontinuous wave- forms are used to provide coagulation effects to tissue.

With reference to FIG. 3, the generator 100 includes a controller 204, a power supply 206, and a RF inverter 208. The power supply 206 may be high voltage, DC power supplies connected to a common AC source (e.g., line voltage) and provide high voltage, DC power to their respective RF inverter 208, which then convert DC power into a RF waveform through active terminal 210 and return terminal 212 corresponding to the selected mode. The active terminal 210 and the return terminal 212 are coupled to the RF inverter 208 through an isolation transformer 214. The isolation transformer 214 includes a primary winding 214a coupled to the RF inverter 208 and a secondary winding 214b coupled to the active and return terminals 210 and 212.

RF energy for energizing a bipolar electrosurgical instru- ment, i.e., forceps 30, is delivered through the ports 114 and 116, each of which is coupled to the active terminal 210 and the return terminal 212. The generator 100 may include a plurality of steering relays or other switching devices con- figured to couple the active terminal 210 and the return terminals 212 to various ports 110, 112, 114, 116, 118 based on the combination of the electrosurgical instruments being used.

The RF inverter 208 is configured to operate in a plurality of modes, during which the generator 100 outputs corre- sponding waveforms having specific duty cycles, peak volt- ages, crest factors, etc. It is envisioned that in other embodi- ments, the generator 100 may be based on other types of suitable power supply topologies. RF inverter 208 may be a resonant RF amplifier or non-resonant RF amplifier, as shown. A non-resonant RF amplifier, as used herein, denotes an amplifier lacking any tuning components, i.e., conduc- tors, capacitors, etc., disposed between the RF inverter and the load, e.g., tissue.

The controller 204 may include a processor (not shown) operably connected to a memory (not shown). The controller 204 is operably connected to the power supply 206 and/or RF inverter 208 allowing the processor to control the output of the RF inverter 208 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to the controller 204. The controller 204 then controls the power supply 206 and/or RF inverter 208, which adjust the DC and/or RF waveform, respectively.

The generator 100 according to the present disclosure may also include a plurality of sensors 216, each of which monitors output of the RF inverter 208 of the generator 100. The sensor 216 may be any suitable voltage, current, power, and impedance sensors. The sensors 216 are coupled to leads 220a and 220b of the RF inverter 208. The leads 220a and 220b couple the RF inverter 208 to the primary winding 214a of the transformer 214. Thus, the sensors 216 are configured to sense voltage, current, and other electrical properties of energy supplied to the active terminal 210 and the return terminal 212.

In further embodiments, the sensor 216 may be coupled to the power supply 206 and may be configured to sense properties of DC current supplied to the RF inverter 208. The controller 204 also receives input (e.g., activation) signals from the display 120, the input controls 122 of the generator 100 and/or the instruments 12 and 14. The con- troller 204 adjust power outputted by the generator 100 and/or perform other control functions thereon in response to the input signals.

The RF inverter 208 includes a plurality of switching elements 228a-228d, which are arranged in an H-bridge topology. In embodiments, RF inverter 208 may be config- ured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicon carbide, or any other suitable wide bandgap materials.

The controller 204 is in communication with the RF inverter 208, and in particular, with the switching elements 228a-228d. Controller 204 is configured to output control signals, which may be pulse-width modulated ("PWM") signals, to switching elements 228a-228d. In particular, controller 204 is configured to modulate a control signal supplied to switching elements 228a-228d of the RF inverter 208. The control signal provides PWM signals that operate the RF inverter 208 at a selected carrier frequency. Addi- tionally, controller 204 are configured to calculate power characteristics of output of the RF inverter 208 of the generator 100, and control the output of the generator 100 based at least in part on the measured power characteristics including, but not limited to, voltage, current, and power at the output of RF inverter 208.

Figure 4:
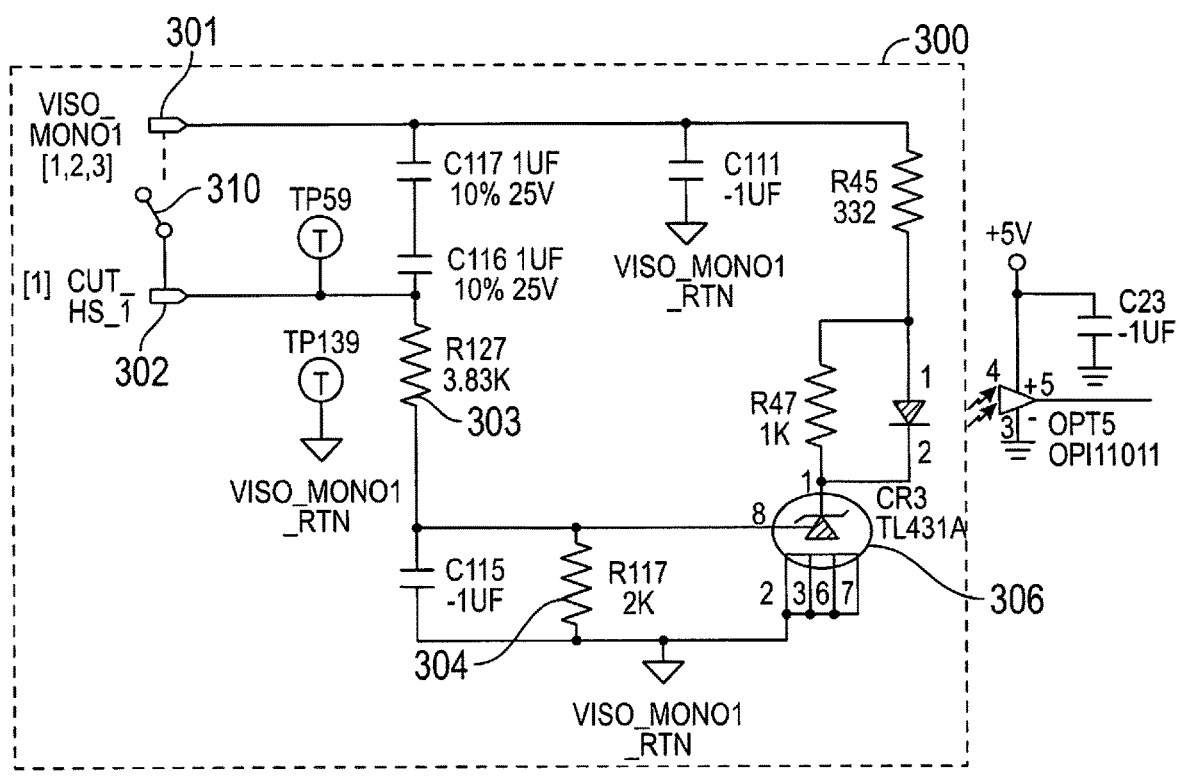
FIG. 4 is an electrical schematic diagram of a multiplexer circuit according to one embodiment of the present disclosure.

The generator 100 is configured to receive switching signals from one or more switches disposed in the forceps 30, such as a switch that is actuated by the button 42, which is used to disable and enable output of the generator 100. With reference to FIG. 4, the generator 100 includes a detection circuit 300 having a first connection 301 and a second connection 302, which are coupled to a switch 310, which may be actuated by the button 42. The detection circuit 300 may be a resistor divider network and includes a first resistor 303 and a second resistor 304 having first and second resistances. The electrosurgical generator 200 includes a signal processor 306, which may be a voltage comparator, coupled to each of the first and second resistors 303 and 304 and is configured to output an activation signal based on the resistance of the detection circuit 300. Multiple switches can be electrically coupled to multiple resistors, such that different combinations of the resistors output different resistance values, which the signal processor 306 then outputs one of a plurality of control signals based on the resistance value.

Figure 5:
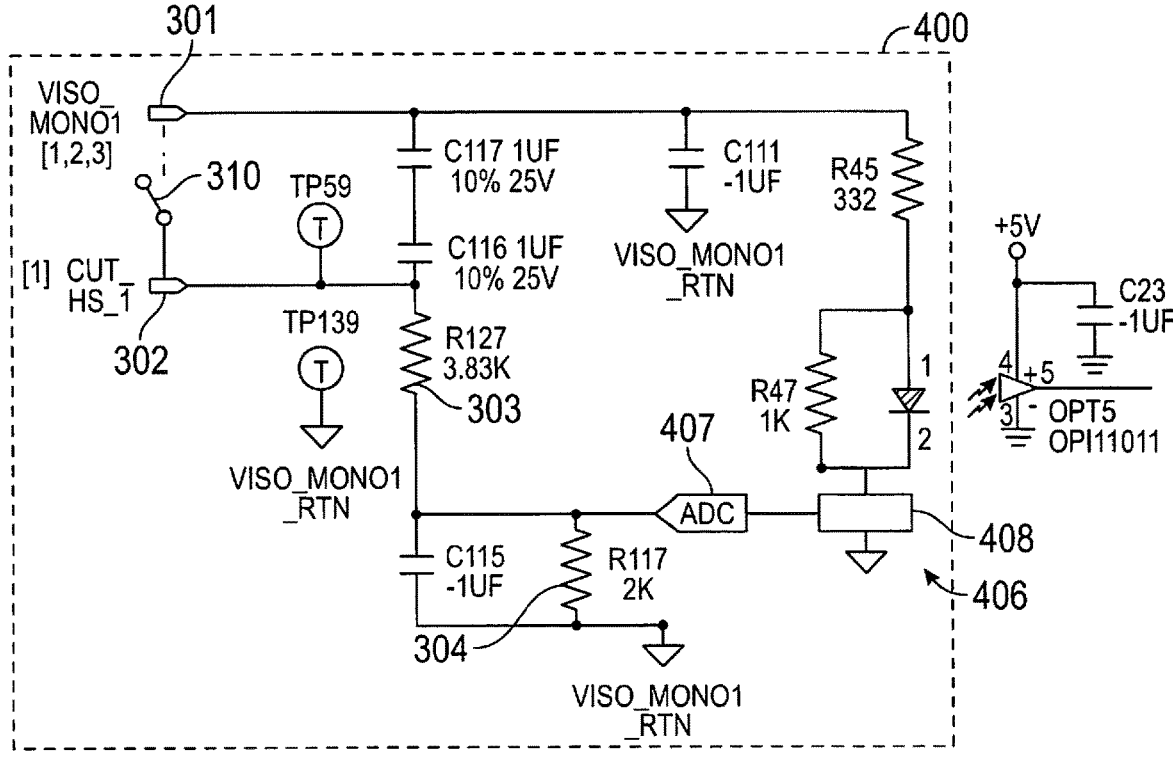
FIG. 5 is an electrical schematic diagram of a multiplexer circuit according to another embodiment of the present disclosure.

FIG. 5 shows another embodiment of a detection circuit 400, which is substantially similar to the detection circuit 300. The signal processor 306 of the electrosurgical generator 200 is replaced with a signal processor 406, which is a combination of an analog-to-digital converter (ADC) 407 and a digital processor 408, which provides more control over the voltage signals of the detection circuit 400. In embodiments, the digital processor 408 may be configured to adjust voltage thresholds, provide filtering, and detect hysteresis.

With reference to FIG. 1, the forceps 30 includes a plurality of switches, namely, a first (i.e., main) switch 500, a second switch 502, and a third switch 504. The first switch 500 is actuated by pressing of the button 42, which is used to activate the generator 100 to apply electrosurgical energy to the tissue grasped between the jaw members 33 and 35. The second switch 502 is coupled to one of the jaw members 33 and 35 and is actuated when the jaw members 33 and 35 are in the closed position. The third switch 504 is coupled to lever 40 and is actuated by the lever 40 as the lever 40 is moved to close the jaw members 33 and 35 and clamp the tissue therebetween. More specifically, the third switch 504 may be coupled to the handle 41 such that the third switch 504 is actuated by the lever 40 being in a closed position relative to the handle 41.

Figures 6, 7:
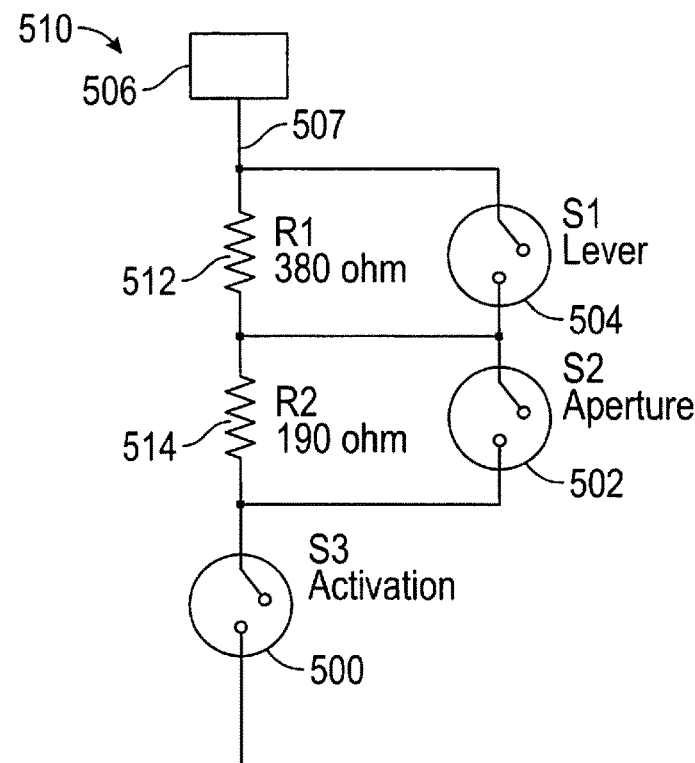
FIG. 6 is an electrical schematic diagram of a multiplexer circuit coupled to a plurality of switches disposed in an electrosurgical device of FIG. 1 according to one embodiment of the present disclosure.
FIG. 7 is a table illustrating a plurality of input signals from the voltage network of FIG. 6 according to the present disclosure.

With reference to FIG. 6, a multiplexer circuit 510 includes the first, second, and third switches 500, 502, 504 coupled to a first and second resistors 512 and 514. The multiplexer circuit 510 may be a resistor divider network and may be similar to the detection circuit 300 or the detection circuit 400 and includes a signal processor 506, which may be similar to either one of the signal processor 306 or 406. The multiplexer circuit 510 transmits switch inputs over a common transmission line 507, thereby acting as a multiplexer for multiple switch inputs. Activation of one or more of the first, second, and third switches 500, 502, 504 outputs a unique voltage signal due to different combination of the first and second resistors 512 and 514 being included in the circuit of the multiplexer circuit 510. As shown in FIG. 6, in order to determine the state of switches 502 and 504, the switch 500 needs to be closed. In embodiments, multiplexer circuit 510 may be configured to place the switch 500 such that the switch 500 may be open or closed while still enabling determination of the state of the switches 502 and 504.

The unique voltage signal is processed by the signal processor 506 according to a truth table shown in FIG. 7. Accordingly, only when the signal processor 506 determines that a specific combination of the first, second, and third switches 500, 502, 504 is activated, the signal processor 506 outputs an activation signal to energize the generator 100 in a corresponding electrosurgical mode. Each of the first, second, and third switches 500, 502, 504 is activated in response to the actuation of the button 42, the handle 41 being in the closed position, and the jaw members 33 and 35 being in the closed position.

The electrosurgical generator 200 is configured to output energy according to one of a plurality of electrosurgical modes based on activation of a specific combination of the first, second, and third switches 500, 502, 504. If only the button 42 is pressed and the first switch 500 is activated, the electrosurgical generator 200 outputs energy in a first electrosurgical mode, e.g., cutting or coagulation. If all of the first, second, and third switches 500, 502, 504 are activated, the electrosurgical generator 200 determines that the jaws 33 and 35 are grasping tissue, the lever 40 is closed, and the button 42 is pressed, indicating to the electrosurgical generator 200 to output energy according to a second electrosurgical output, e.g., a tissue sealing algorithm. Thus, to seal tissue, the forceps 30 is not energized until all three of the switches 500, 502, 504 are closed (i.e., conditions are met). Once the signal processor 506 determines that one of the suitable combinations of the switches 500, 502, 504, has been activated, the controller 204 then receives the activation signal from the signal processor 506 and controls the power supply 206 and the RF inverter 208 to output electrosurgical energy according to a corresponding electrosurgical mode.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical system comprising:
an electrosurgical device including a pair of opposing jaw members movable between an open jaw position and a closed jaw position, and a multiplexer circuit for outputting a voltage signal, the multiplexer circuit comprising:
a main switch for activating a supply of electrosurgical energy;
a second switch configured to actuate when the pair of opposing jaw members is in the closed jaw position;
a third switch configured to activate based on a position of a movable component on the electrosurgical device;
one or more resistors coupled to the main switch, the second switch, and the third switch to at least partially define the voltage signal; and
a signal processor configured to determine, based on the voltage signal, a switch combination comprising a switch state for each of the main switch, the second switch, and the third switch; and
an electrosurgical generator coupled to the electrosurgical device, the electrosurgical generator configured to generate an electrosurgical output in response to the switch combination.

2. The electrosurgical system according to claim 1, wherein the second switch is disposed on one jaw member of the pair of opposing jaw members for actuation when the pair of opposing jaw members are in the closed jaw position.

3. The electrosurgical system according to claim 1, wherein the movable component comprises a lever movable between an open lever position and a closed lever position to move the pair of opposing jaw members between the open jaw position and the closed jaw position, respectively.

4. The electrosurgical system according to claim 3, wherein the electrosurgical device includes a handle, and the third switch is disposed on the handle and is actuated by the lever being in the closed lever position.

5. The electrosurgical system according to claim 1, wherein the signal processor is further configured to output an activation signal for the electrosurgical generator based on the voltage signal.

6. The electrosurgical system according to claim 5, wherein the signal processor includes a voltage comparator.

7. The electrosurgical system according to claim 5, wherein the signal processor includes an analog-to-digital converter and a digital processor configured to process an output signal from the converter.

8. The electrosurgical system according to claim 5, wherein the electrosurgical generator further includes a controller coupled to the signal processor, the controller configured to output a control signal in response to the activation signal.

9. The electrosurgical system according to claim 8, wherein the electrosurgical generator further includes:
   a power supply configured to output a direct current; and
   a radio frequency inverter coupled to the power supply and configured to generate the electrosurgical output by inverting the direct current.

10. The electrosurgical system according to claim 9, wherein the controller is further configured to output the control signal to the radio frequency inverter to generate the electrosurgical output.

11. An electrosurgical system comprising:
   an electrosurgical device including a pair of opposing jaw members movable between an open jaw position and a closed jaw position, and a multiplexer circuit for outputting a voltage signal, the multiplexer circuit comprising:
      a first switch, a second switch, and a third switch, wherein the voltage signal is at least partially defined by a switch combination comprising a switch state for each of the first switch, the second switch, and the third switch;
      a lever coupled to the third switch and movable between an open lever position and a closed lever position, wherein the lever is configured to actuate the third switch in the closed lever position; and
      a signal processor configured to:
         determine the switch combination based on the voltage signal; and
         output an activation signal for an electrosurgical generator based on the switch combination.

12. The electrosurgical system according to claim 11, further comprising:
   an electrosurgical generator coupled to the electrosurgical device, the electrosurgical generator configured to generate an electrosurgical output in response to the switch combination.

13. The electrosurgical system according to claim 12, wherein the electrosurgical generator further includes a controller coupled to the signal processor, the controller configured to output a control signal in response to the activation signal.

14. The electrosurgical system according to claim 11, wherein the first switch is configured for activating a supply of electrosurgical energy.

15. The electrosurgical system according to claim 14, wherein the lever is operably coupled to the pair of opposing jaw members for moving between the open jaw position and the closed jaw position.

16. The electrosurgical system according to claim 15, wherein the lever open position and the lever closed position correspond to the respective open jaw position and closed jaw position.

17. A method for controlling an electrosurgical generator, the method comprising:
   actuating a lever between an open lever position and a closed lever position to move a pair of opposing jaw members between an open jaw position and a closed jaw position;
   activating a jaw switch when the pair of opposing jaw members are in the closed jaw position;
   activating a lever switch when the lever is in the closed lever position;
   activating a main switch by pressing a button;
   determining a type of output to be generated by the electrosurgical generator based on activation of the lever switch and the jaw switch; and
   activating an electrosurgical generator to output the determined output in response to activation of the main switch.

18. The method according to claim 17, further comprising:
   determining whether each of the jaw switch, the lever switch, and the main switch is activated based on a voltage signal output by a multiplexer circuit.

\* \* \* \* \*